(12) United States Patent
Lam et al.

(10) Patent No.: US 6,703,524 B2
(45) Date of Patent: Mar. 9, 2004

(54) ORGANOSELENIUM COMPOUNDS FOR CANCER CHEMOPREVENTION

(75) Inventors: Luke K. T. Lam, North Oaks, MN (US); Nayaz Ahmed, Lauderdale, MN (US)

(73) Assignee: LKT Laboratories, Inc., St. Paul, MN (US)

( * ) Notice: Subject to any disclaimer, the term of this patent is extended or adjusted under 35 U.S.C. 154(b) by 0 days.

(21) Appl. No.: 10/081,297

(22) Filed: Feb. 20, 2002

(65) Prior Publication Data

US 2002/0165215 A1 Nov. 7, 2002

Related U.S. Application Data

(60) Provisional application No. 60/270,116, filed on Feb. 20, 2001.

(51) Int. Cl.$^7$ ............................................. C07C 395/00
(52) U.S. Cl. ...................................................... 562/899
(58) Field of Search ........................................ 562/899

(56) References Cited

U.S. PATENT DOCUMENTS

| | | |
|---|---|---|
| 4,938,949 A | 7/1990 | Borch et al. |
| 6,166,003 A | 12/2000 | Lam |

OTHER PUBLICATIONS

Anderson, "Determination of Glutathione and Glutathione Disulfide in Biological Systems," *Meth. Enzymol.*, 1985; 113:548–564.

Ashton et al., "The Self–Assembly and Dynamic Properties of Thiophene–Containing [2]Catenanes," *Synthesis*, 1994 Dec.; 12:1344–1352.

Ausbel et al., eds., *Current Protocols in Molecular Biology*, vol. 1, Unit 2.2, John Wiley & Sons, New York, 1990, Cover page, Publication page, Table of Contents and Unit 2.2.

Bird, "Observation and quantification of aberrant crypts in the murine colon treated with a colon carcinogen: preliminary findings," *Cancer Lett.*, 1987; 37:147–151.

Chesseaud, "The Role of Glutathione and Glutathion S–transferases in the Metabolism of Chemical Carcinogens and other Electrophilic Agents," *Adv. Cancer. Res.*, 1979; 29:175–274.

Chung et al., "Effects of dietary indoles and isothiocyanates on N–nitrosodimethylamine and 4–(methylnitrosamino)–1–(3–pyridyl)–1–butanone α–hydroxylation and DNA methylation in rat liver," *Carcinogenesis*, 1985 Apr.; 6(4):539–543.

Damani et al., "Chapter 4: Oxidative Metabolsim of Heterocyclic Ring Systems," *Metabolic basis of detoxification*, Jakoby et al., eds, Academic Press, Oxford, 1983; 69–89.

Damani, "Chapter 7: Oxidation at Nitrogen Centers," *Metabolic basis of detoxification*, Jakoby et al., eds, Academic Press, Oxford, 1983; 127–148.

(List continued on next page.)

*Primary Examiner*—Amelia Owens
(74) *Attorney, Agent, or Firm*—Mueting, Raasch & Gebhardt, P.A.

(57) ABSTRACT

A compound containing an alkylene selenocyanate or an alkylene isoselenocyanate moiety effective to prevent the occurrence or progression of cancer or a precancerous condition. The compound can be provided and administered in the form of a pharmaceutical composition, a cosmetic, a food additive, supplement, or the like. Methods for synthesis and use of the chemopreventive compound of the invention are also provided.

20 Claims, 4 Drawing Sheets

OTHER PUBLICATIONS

El–Bayoumy et al., "Inhibition of 7,12–Dimethylbenz(a)anthracene–induced Tumors and DNA Adduct Formation in the Mammary Glands of Female Sprague–Dawley Rats by the Synthetic Organoselenium Compound, 1,4–Phenylenebis(methylene)selenocyanate," *Cancer Res.*, 1992; 52(9):2402–2407.

El–Bayoumy et al., "Chemoprevention of Cancer by Organoselenium Compounds," *Cell. Biochem.*, 1995; 22:92–100.

El–Bayoumy, "Effects of Organoselenium Compounds on Induction of Mouse Forestomach Tumors by Benzo(a)pyrene," *Cancer Res.*, 1985 Aug.; 45(8):3631–3635.

El–Bayoumy et al., "Inhibition of 4–(methylnitrosamino)–1–(3–pyridyl)–1–butanone tumorigenicity in mouse lung by the synthetic organoselenium compound, 1,4–phenylenebis(methylene)selenocyantate," *Carcinogenesis*, 1993 Jun.; 14(6):1111–1113.

Ellman, "Tissue Sulfhydryl Groups," *Arch. Biochem. Biophys.*, 1959; 82:70–77.

Frejd et al., "Selenium–Containing Pancreatic Imaging Agents, Synthesis of β–2–and β–3–Selenienylalanine (1)," *J. Heterocylic Chem.*, 1980; 17:759–761.

Goodwin et al., "Selenium and Glutathione Peroxidase Levels in Patients with Epidermoid Carcinoma of the Oral Cavity and Oropharynx," *Cancer*, 1983 Jan. 1; 51(1):110–115.

Guo et al., "Effects of phenethyl isothiocyanate, a carcinogenesis inhibitor, on xenobiotic–metabolizing enzymes and nitrosamine metabolism in rats," *Carcinogenesis*, 1992 Dec.; 13(12):2205–2210.

Habig et al., "Glutathione S–Transferases," *J. Biol. Chem.*, 1974 Nov. 25; 249(22):7130–7139.

Hecht et al., "Comparative Tumorigenicity and DNA Methylation in F344 Rats by 4–(Methylnitrosamino)–1–(3–pyridyl)–1–butanone and N–Nitrosodimethylamine," *Cancer Res.*, 1986 Feb.; 46:498–502.

Hecht et al., "Tobacco–specific nitrosamines, an important group of carcinogens in tobacco and tobacco smoke," *Carcinogenesis*, 1988 Jun.; 9(6):875–884.

Henriksen et al., "One–Step Synthesis of Alkyl and Aryl Isoseleno–cyanates from Primary Amines," *Synthesis*, 1976 Aug.; 8:519–521.

Hoffmann et al., "Nicotine–derived N–Nitrosamines and Tobacco–related Cancer: Current Status and Future Directions," *Cancer Res.*, 1985 Mar.; 45(3):935–944.

Hojjatie et al., "Synthesis and Multinuclear NMR Characterizations of Some [3.3]Diselena– and [4.4]Tetraselenacyclophanes," *Tetrahedron*, 1989; 45(6):1611–1622.

Ip et al., "Cancer chemoprevention by aliphatic selenocyanates; effect of chain length on inhibition of mammary tumors and DMBA adducts," *Carcinogeneis*, 1995 Jan.; 16(1):35–38.

Jacob et al., "Rat liver microsomal ring– and S–oxidation of thiaarenes with central or peripheral thiophene rings," *Toxicology*, 1991: 67:181–194.

Jakoby et al., eds., *Metabolic Basis of Detoxication: Metabolism of Functional Groups*, Academic Press, New York, 1982; Cover pg., Publication pg., and Table of Contents. (5 pgs.).

Katritzky et al., eds., *Comprehensive Heterocyclic Chemistry*, Pergamon Press, Oxford, 1984; 4(3):pvii–vii.

Kawamori et al.,"Evaluation of benzyl selenocyanate glutathione conjugate for potential chemopreventive properties in colon carcinogenesis," *Int. J. Oncol.*, 1998 Jul.; 13(1):29–34.

Kemal, "Importance of Heterocycles in Biochemical Pathways," *Comprehensive Heterocylic Chemistry vol. 1*, Katritzkey et al., eds., Perman Press, 1997, pgs. 247–268.

Kjaer, "Chapter 34: Naturally occurring isothiocyanates and their parent glycosides," in *Organic Sulfur Compounds*, Kharasch ed., Pergamon Press, New York, 1961; 409–420.

Krisnaswamy et al., "A case control study of selenium in cancer," *Indian J. Med. Res. Sect. B.*, 1993; 98:124–128.

Lam, "Cancer Chemoprevention by Sulfur Compounds," Grant Abstract, Grant No. 24836 Agency Code: SBIR [Dialog: File 266:FEDRIP]. Health and Human Services, 1994. [retrieved on Aug. 12, 2002]. 1 pg.

Lam et al., "Chapter 22: Inhibition of Chemically Induced Carcinogenesis by 2–n–Heptylfuran and 2–n–Butyltiophene from Roast Beef Aroma," *Sulfur compounds in foods*, Mussinan et al., eds., ACS Symposium Series 564, pp. 278–291, 1994.

Lam et al., "Effects of Citrus Limonoids on Glutathion S–Transferase Activity in Mice," *J. Agric. Food Chem.*, 1989; 37(4):878–880.

Lam et al., "Inhibition of Benzo[α]pyrine–Induced Forestomach Neoplasia in Mice by Citrus Limonoids," *Nutr. Cancer*, 1989; 12(1):43–47.

Lam et al., "Inhibitory effects of 2–n–Heptylfuran and 2–n–Butylthiophene on Benzo[α]Pyrene–Induced Lung and Forestomach Tumorigenesis in A/J Mice," *Nutr. Cancer*, 1992; 17(1):19–26.

Lowry et al., "Protein Measurements with the Filin Phenol Reagent," *J. Biol. Chem.*, 1951; 193:265–275.

Mac Leod et al., "Capillary Gas Chromatography–Mass Spectrometric Analysis of Cooked Ground Beef Aroma," *J. Food Sci.*, 1986; 51(6):1427–1434.

Maga, "Potato Glycoalkaloids," *CRC Critical Reviews in Food Science and Nutrition*, 1980 Jul.; 12(4):371–405.

Mautner et al., "The Synthesis and Antineoplastic Properties of Selenoguanine, Selenocytosine and Related Compounds," *J. Med. Chem.*, 1963 Jan.; 6:36–39.

Mautner et al., "A Comparative Study of 6–Selenopurine and 6–Mercaptopurine in the *Lactobacillus casei* and Ehrlich Ascites Tumor Systems," *Biochem. Pharmacol.*, 1959 Jan.; 1(3):169–173.

McLellan et al., "Aberrant Crypts: Potential Preneoplastic Lesions in the Murine Colon," *Cancer Res.*, 1988 Nov. 1; 48(21):2311–2315.

McLellan et al., "Specificity Study to Evaluate Induction of Aberrant Crypts in Murine Colons," *Cancer Res.*, 1988 Nov. 1; 48(21):6183–6186.

Min et al., "Preliminary Identification of Volatile Flavor Compounds in the Neutral Fraction of Roast Beef," *J. Food Sci.*, 1979; 44(3):639–642.

Morimoto et al., "N,N–Bis(trimethylsilyl)methosymethylamine as a Convenient Synthetic Equivalent of $^+CH_2NH_2$: Primary Aminomethylation of Organometallic Compounds," *J. Chem. Soc. Chem. Commun.*, 1984; 12:794–795.

Morse et al., "Effects of alkyl chain length on the inhibition of NNK–induced lung neoplasia in A/J mice by arylakyl isothiocyanates," *Carcinogenesis*, 1989; 10(9):1757–1759.

Morse et al., "Effects of Indole–3–carbinol on Lung Tumorigenesis and DNA Methylation Induced by 4–(Methylnitrosamino)–1–(3–pyridyl)–1 butanone (NNK) and on the Metabolism and Disposition of NNK in A/J Mice," Cancer Res., 1990; 50:2613–2617.

Morse et al., "Inhibition of 4–(Methylnitrosamino)–1–(2–pyridyl)–1–butanone–induced DNA Adduct Formation and Tumorigenicity in the Lung of F344 Rats by Dietary Phenethyl Isothiocyanate," Cancer Res., 1989 Feb. 1; 49(3):549–553.

Mulder, "Chapter 13: Conjugation of Phenols," Metabolic basis of detoxification, Jakoby et al., eds, Academic Press, Oxford, 1983; 247–269.

Murphy et al., "Rat liver metabolism of Benzo[b]naptho[2,1–d]thiophene," Chem. Res. Toxic., 1992 Feb.; 5(3):491–495.

Nayini et al., "Chemoprevention of experimental mammary carcinogenesis by the synthetic organoselenium compound, benzylselenocyanate, in rats," Carcinogenesis, 1989; 10:509–512.

Nebert et al., "Role of the Ah Receptor and the Dioxin–Inducible [Ah] Gene Battery in Toxicity, Cancer, and Signal Transduction," Am. NY Acad. Sci.: Immunomodulating Drugs, Georgiev et al., eds., The New York Academy of Sciences, New York, 1993; 385:624–640.

Pampalone et al., "The Preparation of 1–Aryl–2–(2–Thienyl)Ethylenes," Org. Pre. and Procedures, 1969 Jul; 1(3):209–212.

Reddy et al., "Chemoprevention of Colon Carcinogenesis by Dietary Organoselenium, Benzylselenocyanate, in F344 Rats," Cancer Res., 1987 Nov. 15: 47:5901–5904.

Reddy et al., "Chemoprevention of Colon Cancer by Organoselenium Compounds and Impact of High– or Low–Fat Diets," J. Natl. Cancer Inst., 1997 Apr. 2; 89(7):506–512.

Reddy et al., "Chemoprevention of Colon Carcinogenesis by the Synthetic Organoselenium Compound 1,4–Phenylenebis(methylene)selenocyanate," Cancer Res., 1992 Oct. 15; 52(20):5635–5640.

Rivenson et al., "Induction of Lung and Exocrine Pancreas Tumors in F344 Rats by Tobacco–specific and Areca–derived N–Nitrosamines," Cancer Res., 1988 Dec. 1; 48(23):6912–6917.

Ronai et al., "Effects of organic and inorganic selenium compounds on rat mammary tumor cells," Int. J. Cancer, 1995; 63:428–434.

Rogers et al., "A Case–Control Study of Oral Cancer and Pre–Diagnostic Concentrations of Selenium and Zinc in Nail Tissue," Int. J. Cancer., 1991 May 10; 48(2):182–188.

Rouseff et al., "Determination of Limonin and Related Limonoids in Citrus Juices by High Performance Liquid Chromatogrpahy," Anal. Chem., 1980 Jul.; 52(8):1228–1233.

Samaha et al., "The Role of Apoptosis in the Modulation of Colon Carcinogenesis by Dietary Fat and by the Organoselenium Compound 1,4–Phenylenebis(methylene)selenocyanate," Cancer Epidemiology, Biomarkers & Prevention, 1997 Sep.; 6:699–704.

Scheline, Mammalian metabolism of plant xenobiotics, Academic Press, London, 1978; Cover page, Publication page and Table of Contents only (5 pgs.).

Schrauzer et al., "Cancer Mortality Correlation Studies–III: Statistical Associations with Dietary Selenium Intakes," Bioinorg. Chem., 1977: 7(1):23–31.

Shankel et al., Antimutagenesis and Anticarcinogenesis Mechanisms, Plenum Press, New York, 1986; Cover page, Publication page, and Table of Contents only (6 pgs.).

Siller–Cepeda et al., "High performance liquid chromatography analysis of reduced and oxidized glutathione in woody plant tissues," Plant Cell Physiol., 1991; 32(8):1179–1185.

Suzuki, "A Photochemical Route to Some Substituted Benzyl Isoselenocyanates," Synthesis, 1979 Sep.; 9:705–707.

Tanaka et al., "1,4–Phenylenebis(methylene)selenocyanate Exerts Exceptional Chemopreventitive Activity in Rat Tongue Carcinogenesis," Cancer Res., 1997 Sep. 1; 57(17):3644–3648.

Wattenberg, "Inhibition of Carcinogen–induced neoplasis by sodium cyanate, tert–Butyl Isocyanate, and Benzyl Isothiocyanate administered subsequent to carcinogen exposure," Cancer Res., 1981 Aug.; 41:2991–2994.

Wattenberg, "Inhibitory effects of benzyl isothiocyanate administered shortly before diethylnitrosamine or benzo[α] pyrene on pulmonary and forestomach neoplasia in A/J/ mice," Carcinogenesis, 1987; 8(12):1971–1973.

Willet et al., "Prediagnostic serum selenium and risk of cancer," The Lancet, 1983, Jul. 16; 2:130–134.

Yuryev et al., "The Chemistry of Selenophene V. Selenophene–2–aldehyde, selenophene–2–carbinol and selenophene–2–acrylic acid," J. Gen. Chm. (USSR), 1957 Jan.; 27(1):201–204.

Yuryev et al., "Chemistry of Selenophene IX. Condensation of Selenophene–2–Carboxyaldehyde with methyl ketones, synthesis and reactions of 2–methylselenophene–5–carboxaldehyde," J. Gen. Chm. ( USSR), 1957 Nov.; 27(11):3193–3197.

Zakim et al., "Techniques for the Characterization of UDP–Glucuronyltransferase, Glucose–6–Phosphatase, and Other Tightly–Bound Microsomal Enzymes," Methods of Biochemical Analysis, Glick ed., 1973; 21:1–37.

Zhang et al., "A major inducer of anticarcinogenic protective enzymes from brocolli: Isolation and elucidation of structure," Proc. Natl Acad. Sci. USA, 1992 Mar.; 89(2403):2399.

Zheng et al., "Chemoprevention of Benzo[α]pyrene–Induced Forestomach Cancer in Mice by Natural Phthalides from Celery Seed Oil," Nutr. Cancer., 1993; 19(1):77–86.

Zheng et al., "Short Communication: Inhibition of benzo[α] pyrene–induced tumorigenesis by myristicin, a volatile aroma constituent of parsley leaf oil," Carcinogenesis, 1992 Oct.; 13(10):1921–1923.

Ahmed, Nayaz, "Bifunctional Organoselenium compounds in Chemoprevention", Grant Abstract, Grant Number 1R43CA079266–01A1 [online]. National Cancer Institute, project dates May 7, 1999–May 6, 2000 [retrieved on Nov. 7, 2002]. Retrieved from the Internet: URL: http://commons.cit.nih.gov/crisp3/CRISP_LIB.getdoc?textkey= 2867542&p_gran t_num=1R43CA079266–01A1&p_ query=&ticket=2234339&p_audit_session_id =11269607&p_keywords=, 1 page.

Wherein:

R¹ is H, and R² is  , (a)                 (b)

R¹ is H, and R² is  , (c)                 (d)

R¹ is H, and R² is  , (e)                 (f)

R¹ is H, and R² is  , (g)                 (h)

Z is S, Se, or O
n = 1, 2, 3, 4, 5, 6, 7, 8, 9, 10, 11 or 12
For disubstituted derivatives R¹ = R² ≠ H Z is S, Se, or O
n = 1, 2, 3, 4, 5, 6, 7, 8, 9, 10, 11 or 12

(a)

Z is S, Se, or O
n = 1, 2, 3, 4, 5, 6, 7, 8, 9, 10, 11 or 12

(b)

Z is S, Se, or O
n = 1, 2, 3, 4, 5, 6, 7, 8, 9, 10, 11 or 12

(c)

Z is S, Se, or O
n = 1, 2, 3, 4, 5, 6, 7, 8, 9, 10, 11 or 12

(d)

Z is S, Se, or O
n = 1, 2, 3, 4, 5, 6, 7, 8, 9, 10, 11 or 12       (a)

Z is S, Se, or O
n = 1, 2, 3, 4, 5, 6, 7, 8, 9, 10, 11 or 12       (b)

Z is S, Se, or O
n = 1, 2, 3, 4, 5, 6, 7, 8, 9, 10, 11 or 12       (c)

Z is S, Se, or O
n = 1, 2, 3, 4, 5, 6, 7, 8, 9, 10, 11 or 12       (d)

ORGANOSELENIUM COMPOUNDS FOR CANCER CHEMOPREVENTION

This application claims the benefit of U.S. Provisional Application Serial No. 60/270,116, filed Feb. 20, 2001, which is incorporated herein by reference in its entirety.

STATEMENT OF GOVERNMENT RIGHTS

This invention was made with government support under a Phase I Grant No. 1R43CA79266-01A1 from the National Institutes of Health (National Cancer Institute). The U.S. government has certain rights in this invention.

BACKGROUND OF THE INVENTION

Cancer incidence and mortality have not declined at the same rate as other major causes of death. This suggests that primary prevention, including the use of chemopreventative agents, is a valuable approach to decreasing mortality, as it avoids all the potential shortfalls and difficulties associated with cancer therapy.

Selenium is an essential nonmetallic nutrient in mammals. Its deficiency is associated with increased incidence of leukemia and cancers of bladder, breast, gastrointestinal tract (e.g., colon and rectum), ovary, stomach, lung and prostrate. There is convincing evidence that a dietary supplement of selenium substantially reduces the incidence of a wide variety of cancers in laboratory animals. Higher intake of selenium provides protection by correcting nutritionally deficient status in animals and also increases antitumorigenic activity. El-Bayoumy, *Cancer Res.*, 45:3631–3635 (1985); Reedy et al., *Cancer Res.* 47:5901–5904 (1987); Nayini et al., *Carcinogenesis* 10:509–512 (1989); El-Bayoumy et al., *Cell. Biochem.*, 22:92–100 (1995); El-Bayoumy, "The role of selemium in cancer prevention," in: *Cancer Principles and Practice of Oncology*, DeVita et al., eds., J.B. Lippincot Co., Phildelphia (1991).

Epidemiological studies in humans also suggest a protective role for selenium in human cancers. Human cancer mortality is lower in areas providing an adequate dietary intake of selenium as estimated from the selenium content in grains and forage crops in various regions of the United States, or the dietary selenium intake as calculated from food consumption data in various countries. Schrauzer et al. *Bioinorg. Chem.* 7:23–31 (1977).

An excess of selenium is associated with toxicity and a large number of health disorders, such as body weight loss, liver damage, splenomegaly, pancreatic enlargement, anemia, hair loss and abnormal nails. The margin between its protective role and adverse effect is very low and depends on the form of selenium being used. For its protective role, the rate of release of selenium from its compound to the selenium pool should be in the range of its required rate of absorption by the biological system.

The search for the best form of selenium for cancer chemoprevention has led to the investigation of a wide variety of selenium forms. Examples of compounds that have been investigated include inorganic salts like sodium selenite, as well as organoselenium compounds such as selenocysteine (a naturally occurring form of selenium) and a number of structurally designed aliphatic and aromatic selenium-containing compounds such as heptylselenocyanate and pentylselenocyanate. Ip et al., *Carcinogenesis* 16:35–38 (1995).

Although inorganic selenium compounds inhibit carcinogenesis, they are toxic. Organic sources of selenium that have been investigated to date, such as the naturally occurring selenium-containing amino acids selenomethionine and selenocysteine which are ingested via cereals, vegetables, and grains, are somewhat more effective than inorganic selenium in cancer prevention but have comparable toxicity. El-Bayoumy, "The role of selenium in cancer prevention," in: *Cancer Principles and Practice of Oncology*, DeVita et al., eds., J. B. Lippincot Co., Philadelphia (1991).

Among the organoselenium compounds investigated to date, the benzene-based compound 1,4-phenylenebis (methylene)selenocyanate (also known as p-xyleneselenocyanate, or p-XSC) is reported to exert the most effective chemopreventative effect on chemically induced carcinogenesis in the mammary glands, colon, and lung of laboratory animals. Reddy et al., *Cancer Res.* 52:5635–5640 (1992); Reddy et al., *J. Natl. Cancer Inst.* 89:506–512 (1997); El-Bayoumy et al., *Cancer Res.* 52:2402–2407 (1992); El-Bayoumy et al., *Carcinogenesis* 14:1111–1113 (1993). Organic compounds having a 5-membered heterocyclic ring substituted with an alkylene isothiocyanate, wherein the heteroatom is sulfur, selenium, or oxygen, have also been described as having cancer chemopreventative activity (U.S. Pat. No. 6,166,003, Lam).

SUMMARY

The invention provides novel organoselenium compounds for use in cancer chemoprevention. In one embodiment, the compound of the invention is a 5-membered heterocyclic ring substituted with an alkylene selenocyanate at least at the 2-position on the ring, as shown in formula I:

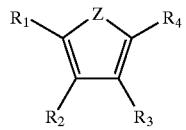

wherein:
$R_1$ is H, (alkylene)-SeCN, or a blocking group;
$R_2$ is H, (alkylene)-SeCN, or a blocking group;
$R_3$ is H, (alkylene)-SeCN, or a blocking group; and
$R_4$ is (alkylene)-SeCN; and
Z is S, Se or O.

Also provided by the invention are cysteine-containing conjugates of the organoselenium compound shown in formula I, wherein the cyanate group (—CN) at one or more of $R_1$, $R_2$, $R_3$ and $R_4$ is replaced with a cysteine or a cysteine-containing peptide such as the tripeptide glutathione (γ-glutamylcysteinylglycine). Preferably, the sulfur atom of the cysteine residue is covalently linked to the selenium atom of the at least one (alkylene)-SeCN moiety. A preferred conjugate is the compound of formula I wherein the cyanate group (—CN) of at least one (alkylene)-SeCN moiety is replaced with a cysteine, an N-acetyl cysteine, a cysteinylglycine, or the tripeptide glutathione.

Preferably, in compounds wherein $R_1=R_4$=methylene-SeCN, at least one of $R_2$ and $R_3$ is not H. However, in pharmaceutical and food additive compositions and in methods of use of the cancer chemopreventive compounds of the invention, the compound can include formula I wherein $R_1=R_4$=methylene-SeCN and $R_2=R_3$=H.

In another embodiment, the compound of the invention is a 5-membered heterocyclic ring substituted with an alkylene isoselenocyanate at least at position 2 on the ring, as shown in formula II:

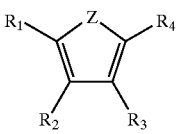

II wherein:
$R_1$ is H, (alkylene)-NCSe, or a blocking group;
$R_2$ is H, (alkylene)-NCSe, or a blocking group;
$R_3$ is H, (alkylene)-NCSe, or a blocking group;
$R_4$ is (alkylene)-NCSe; and
Z is S, Se or O.

Also provided by the invention are cysteine-containing conjugates of the organoselenium compound shown in formula II, wherein the isoselenocyanate group (—NCSe) at one or more of $R_1$, $R_2$, $R_3$ and $R_4$ is replaced with a cysteine-containing moiety having the general formula —N(H)C(Se)$R_5$ wherein $R_5$ is cysteine, a derivative thereof, or a peptide containing cysteine. For example, one or more of $R_1$, $R_2$, $R_3$ and $R_4$ is replaced with —N(H)C(Se)cysteine or —N(H)C(Se)glutathione where $R_5$ is cysteine or glutathione, respectively. Preferably, the sulfur atom of the cysteine residue is covalently linked to the carbon atom of the at least one (alkylene)-NCSe moiety. A preferred conjugate is the compound of formula II wherein the isoselenocyanate group (—NCSe) of at least one (alkylene)-NCSe moiety is replaced with —N(H)C(Se)cysteine, —N(H)C(Se)—N-acetylcysteine, —N(H)C(Se)cysteinylglycine, or —N(H)C(Se)glutathione.

In yet another embodiment, the compound of the invention is a xyleneisoselenocyanate compound as shown in formula III:

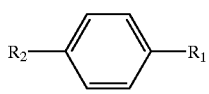

III wherein:
$R_1$ is H, (alkylene)-NCSe, or a blocking group; and
$R_2$ is (alkylene)-NCSe.

The disubstituted form of the compound of formula III, 1,4-phenylenebis(alkylene)selenocyanate, (also known as p-xyleneisoselenocyanate, or p-XISC) is especially preferred.

Also provided by the invention are cysteine-containing conjugates of the organoselenium compound shown in formula III, wherein the isoselenocyanate group (—NCSe) at one or both of $R_1$ and $R_2$ is replaced with a cysteine-containing moiety having the general formula —N(H)C(Se)$R_3$ wherein $R_3$ is cysteine, a derivative thereof, or a peptide containing cysteine. For example, one or both of $R_1$ and $R_2$ is replaced with —N(H)C(Se)cysteine or —N(H)C(Se)glutathione where $R_3$ is cysteine or glutathione, respectively. Preferably, the sulfur atom of the cysteine residue is covalently linked to the carbon atom of the at least one (alkylene)-NCSe moiety. A preferred conjugate is the compound of formula III wherein the isoselenocyanate group (—NCSe) of at least one (alkylene)-NCSe moiety is replaced with —N(H)C(Se)cysteine, —N(H)C(Se)—N-acetylcysteine, —N(H)C(Se)cysteinylglycine or —N(H)C(Se)glutathione.

The term "alkylene" as used herein means a divalent saturated hydrocarbon chain containing one or more carbon atoms. An alkylene can be linear or branched. Examples of linear alkylenes include methylene (—CH$_2$—), ethylene (—CH$_2$—CH$_2$—), propylene (—CH$_2$—CH$_2$—CH$_2$—), butylene (—CH$_2$—CH$_2$—CH$_2$—CH$_2$—) and so on. Examples of branched alkylenes include compounds such as —CH$_2$—CH(CH$_3$)-CH$_2$—, —CH$_2$—CH(CH$_2$CH$_3$)-CH$_2$—, CH$_2$—CH(CH$_3$)-CH$_2$—CH(CH$_3$)-CH$_2$—, —CH$_2$—C(CH$_3$)$_2$—CH$_2$—and the like. The compound of the invention is not intended to be limited by the length of the alkylene chain that connects a selenocyanate (—SeCN) or an isoselenocyanate (—NCSe) group (or conjugate thereof) to the heterocyclic moiety.

Moreover, where the compound contains an alkylene selenocyanate or alkylene isoselenocyanate substituent (or conjugate thereof) at more than one position on the heterocyclic ring, the alkylene functionalities connecting the selenocyanate or isoselenocyanate groups (or conjugates thereof) at the respective ring positions can have different numbers of carbon atoms.

Linear alkylene chain lengths of about 1 to about 20 carbons (C 1-C 20) are preferred for ease of synthesis. Preferably, the alkylene chain length connecting the selenocyanate or isoselenocyanate group (or conjugate thereof) to the heterocyclic moiety is about 1 to about 12 carbons (C 1-C 12), more preferably about 1 to about 6 carbons (C 1-C 6), most preferably about 1 to about 4 carbons (C 1-C 4). For example, a representative compound of the invention is 2-thienyl methyl isoselenocyanate, which has a C, alkylene functionality (i.e., a 1 carbon chain) connecting isoselenocyanate (-NCSe) to the 2-position of the thienyl ring (II, wherein $R_1$=$R_2$=$R_3$=H and $R_4$ is (methylene)-NCSe; and Z=S).

As used herein, the term "heterocyclic ring" refers to a ring structure that contains as a member of the ring at least one noncarbon atom. In the heterocyclic ring of the compound of formula I or formula II, or conjugates thereof, the non-carbon member Z is preferably S, but can alternatively be Se or O.

Where one or more of $R_1$, $R_2$ and $R_3$ is a blocking group, it is not intended to be limited to any particular blocking group, and it should be understood that different blocking groups can be used at different ring positions. A blocking group can be aromatic or aliphatic, and can be linear, branched, or cyclic. A blocking group is preferably an alkyl, alkoxy, aryl, aryloxy, alkylmercapto, alkylene aryl, CX$_3$, or X; wherein X is F, Cl, or Br. Aromatic or aliphatic constituents of a blocking group can be substituted or unsubstituted. More preferably the blocking group is CH$_3$, OCH$_3$, SCH$_3$, CX$_3$ or X; most preferably it is OCH$_3$, SCH$_3$, CF$_3$ or F.

Substituting the 5-position of the ring is desirable in order to enhance the chemopreventive effect of the compound of the invention, for example by slowing metabolism of the ring moiety in a treated subject or by way of a steric effect. Therefore, the compound of formula I, II or III, wherein $R_1$ is (alkylene)-SeCN (in the case of formula I) or (alkylene)-NCSe (in the case of formula II and formula III), cysteine-containing conjugates of either (alkylene)-SeCN or (alkylene)-NCSe, or a blocking group is especially preferred.

Also included in the present invention are methods for making a compound having formula I, formula II, or formula III,-as well as cysteine-containing conjugates thereof.

The present invention further includes a pharmaceutical composition comprising an active ingredient which is a compound of the present invention. Preferred embodiments of the pharmaceutical composition are those that contain preferred embodiments of the compound having formula I, II, or III, or cysteine-containing conjugates thereof, as set forth above. Included in the pharmaceutical composition is, preferably, a pharmaceutically acceptable carrier, which can comprise a pharmaceutically acceptable salt. The pharmaceutical composition is suitable for treatment of an existing condition or for prophylactic use.

Additionally, the compound of the present invention can be incorporated into food or drink as an additive or supplement, or formulated for cosmetic use, as in a body lotion, creme, sunscreen or the like.

The present invention further includes a method for preventing the occurrence or progression of a cancer or a precancerous condition, including cellular changes characterized by neoplasia. The method comprises administering to a mammal a chemopreventive composition comprising the compound the present invention in an amount effective to prevent the occurrence of cancer (carcinogenesis) or a precancerous condition, or to slow or halt the progression of cancer or precancerous conditions. The chemopreventive composition can be administered as a therapeutic to treat an existing condition or as a prophylactic in advance of exposure to a carcinogenic compound or event.

DETAILED DESCRIPTION

Figure 1:
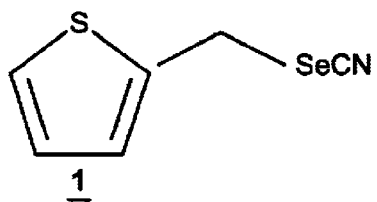
FIG. 1 illustrates the structures of (a) representative selenocyanates of thiophene and selenophene: 1,2-thienyl methylene selenocyanate (TMSC); 2, thienyl-2,5-di-methylene selenocyanate (TDMSC); 3,2-selenophenyl methylene selenocynate (SMSC); and 4, selenophenyl-2,5-di-methylene selenocyanate (SDMSC); and (b) representative isoselenocyanates of thiophene and selenophene: 2-thienyl methylene isoselenocyanate (TMISC); 6, thienyl-2,5-di-methylene isoselenocyanate (TDMISC); 7, selenophenyl-2,5-di-methylene isoselenocyanate (SDMISC); and 8,2-selenopnenyl methylene isoselenocyanate (SMISC).
Figure 1:
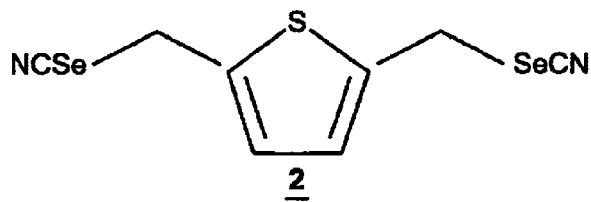
Figure 1:
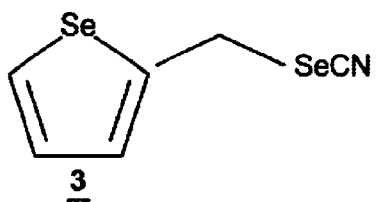
Figure 1:
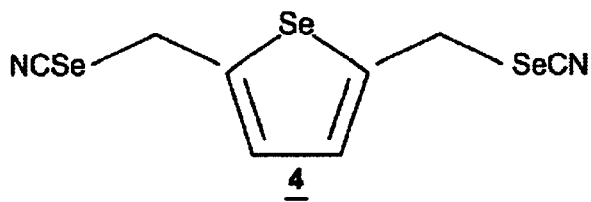
Figure 1:
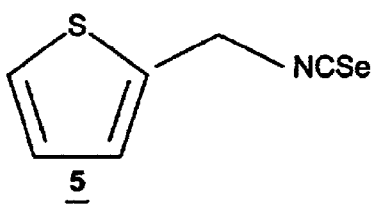
Figure 1:
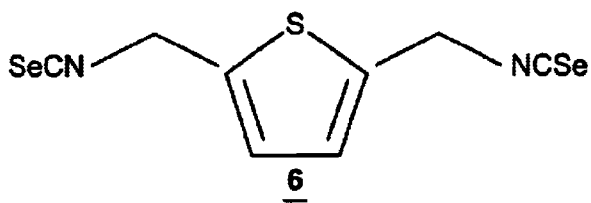
Figure 1:
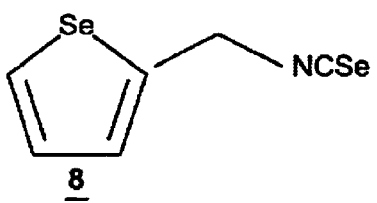
Figure 1:
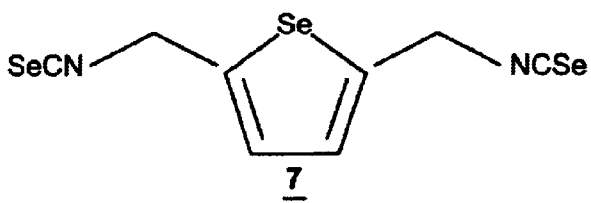

Alkylene selenocyanates and alkylene isoselenocyanates are sometimes referred to in the literature as heterocyclic "alkyl" selenocyanates or isoselenocyanates. They are, however, more accurately termed "alkylene" selenocyanates or isoselenocyanates in that a divalent alkylene chain ($-(CH_2)_n-$), e.g., methylene, ethylene, propylene, butylene and so on) functions as a linker between the selenocyanate ($-SeCN$) or isoselenocyanate ($-NCSe$) and the heterocyclic ring according to the invention. For example, the terms "alkyl isoselenocyanate" and "alkylene isoselenocyanate," can be used interchangeably to mean a $-(CH_2)_n-NCSe$ substituent; accordingly, for example, methyl isoselenocyanate means $-CH_2-NCSe$; butyl isoselenocyanate means $-(CH_2)_4-NCSe$, phenyl butyl isoselenocyanate means Ph-$(CH_2)_4-NCSe$, and so on.

An object of the present invention is to provide a chemopreventive organoselenium compound that has less toxicity, superior activity as an enzyme inducer, and broader inhibitory activity than the reference compound, p-XSC. The potentials of various heterocyclic selenocyanates and isoselenocyanates as chemopreventive agents were evaluated using well-known assays for chemopreventive activity including glutathione sulfotransferase (GST) induction, increased production of glutathione (GSH) and AC inhibition assays, as described in the following examples. Surprisingly, it was found that p-XSC failed to induce a significant increase in glutathione GST activity or to increase the concentration of its mandatory substrate, GSH (see Tables 3 and 4, below). This is a major flaw, as the induction of transcriptionally regulated phase II enzymes such as GST has been recognized as an important mechanism that provides protection against a large number of carcinogens. In addition, GSH itself is a potent detoxifying agent. In contrast to the reference compound p-XSC, the tested compounds were found to be potent inducers of the GST enzyme system.

The 5-membered ring of the compound of the invention can be monosubstituted, disubstituted, trisubstituted, or tetrasubstituted, such that the alkylene selenocyanate or alkylene isoselenocyanate moiety is at one or more of the 2-, 3-, 4-or 5-positions on the ring. The 2-substituted series of compounds, with or without an alkylene selenocyanate or alkylene isoselenocyanate moiety or blocking group at the 5-position, is preferred for use as a chemopreventive agent because it can be synthesized from more readily available starting materials.

In a particularly preferred embodiment, the compound of the invention is a 2,5-disubstituted compound. Thiophene metabolism is believe to occur at the S-atom and the α carbons (2,5-positions) of the molecule (S. Murphy et al., *Chem. Res. Toxic.* 5:491–495 (1992); J. Jacob et al., *Toxicology* 68:181–194(1991))). Without wishing to be bound by theory, it is believed that on the 2-monosubstituted series, metabolic conversion of the ring can still occur at the S atom by way of the 5-position. To slow down and prevent the rate of oxidative metabolism of the compound, the 5-position of ring is preferably blocked by the use of substituents such as $CH_3$, $OCH_3$, $CF_3$ and F groups, or substituted with an alkylene selenocyanate or an alkyleneisoselenocyanate. In addition to blocking the 5-position, these substituents serve as additional steric hindrance near the S atom. The $OCH_3$, $CF_3$ and F groups are preferred as blocking groups.

Particularly preferred compounds for use in the invention illustrated in FIG. 1. Compound 2 (TDMSC) has been reported in Hojjatie et al., *Tetrahedron* 45(6), 1611–1622 (1989).

Conjugating one or more, preferably all, of the alkylene selenocyanate or alkylene isoselenocyanate moieties to cysteine, or to a peptide containing cysteine, such as glutathione, via the sulfur atom of the cysteine residue yields a compound that is more similar than the unconjugated compound to naturally occurring compounds found in cruciferous vegetables, and is thus expected to reduce the potential toxicity of the compound of the invention while retaining efficacy. Thus, in a preferred embodiment, the compound of the invention is a cysteine conjugate or a cysteine-containing peptide conjugate, preferably a glutathione conjugate, of the 2-substituted compound or the 2,5-disubstituted compound.

If the cysteine contains a free amino group and/or a free carboxyl group (i.e., is not located internally within a peptide), the cysteine can be derivatized at the free amino group (as in N-acetyl cysteine) or at the free carboxyl group, or both.

Figure 2:
FIG. 2 illustrates general structures of representative cysteine-containing conjugates of selenocyanates and isoselenocyanates of thiophene and selenophene: (a) cysteine conjugate of a selenocyanate; (b) cysteine conjugate of an isoselenocyanate; (c) N-acetylcysteine conjugate of a selenocyanate; (d) N-acetylcysteine conjugate of an isoselenocyanate; (e) cysteinylglycine conjugate of a selenocyanate; (f) cysteinylglycine conjugate of an isoselenocyanate; (g) glutathione conjugate of a selenocyanate; and (h) glutathione conjugate of an isoselenocyanate.
Figure 2:
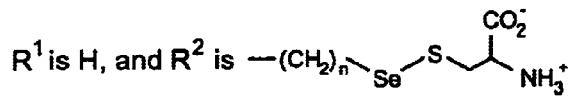
Figure 2:
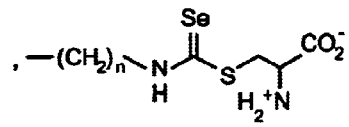
Figure 2:
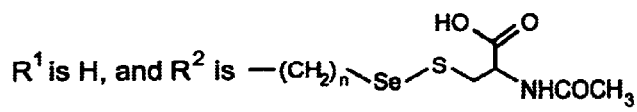
Figure 2:
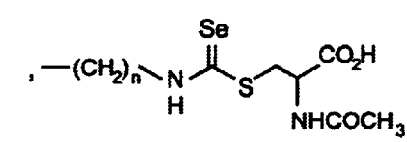
Figure 2:
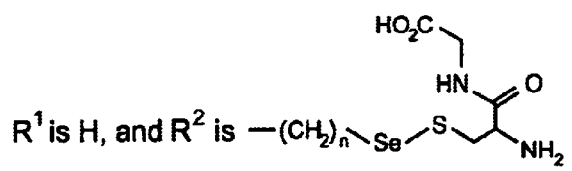
Figure 2:
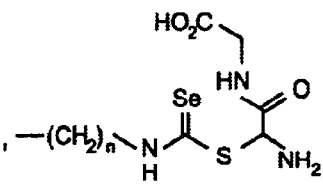
Figure 2:
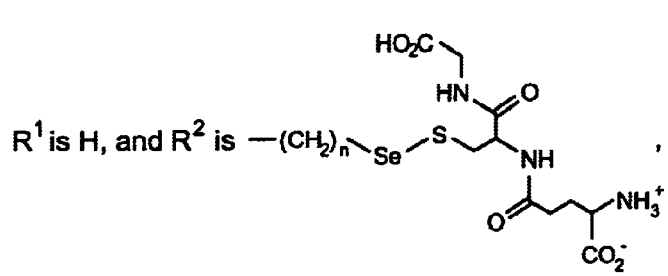
Figure 2:
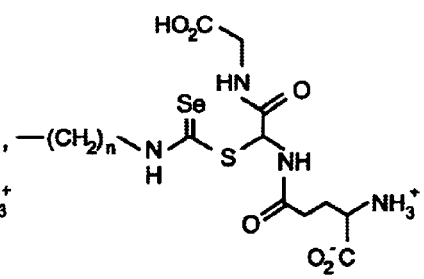
Figure 3:
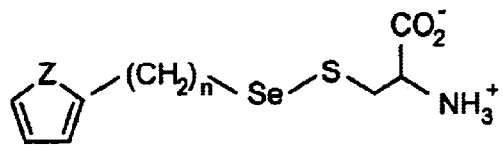
FIG. 3 illustrates general structures of representative cysteine and glutathione conjugates of selenocyanates of monosubstituted and disubstituted heterocyclic compounds: (a) monosubstituted cysteine conjugate; (b) disubstituted cysteine conjugate; (c) monosubstituted glutathione conjugate; and (d) disubstituted glutathione conjugate.
Figure 3:
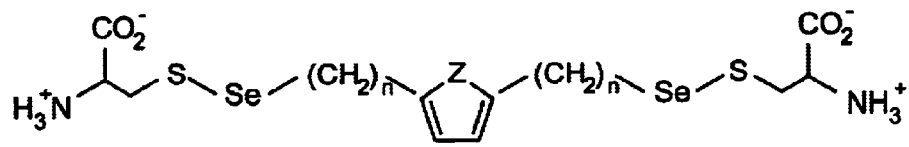
Figure 3:
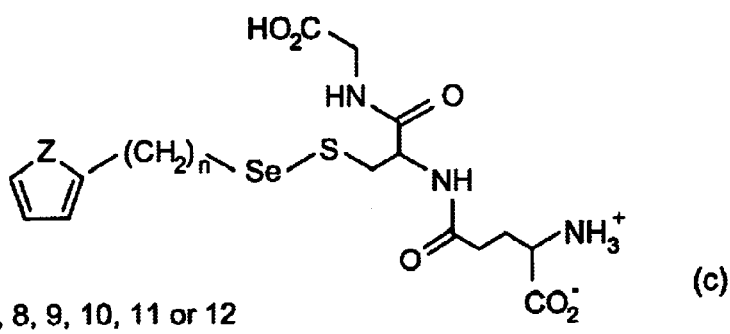
Figure 3:
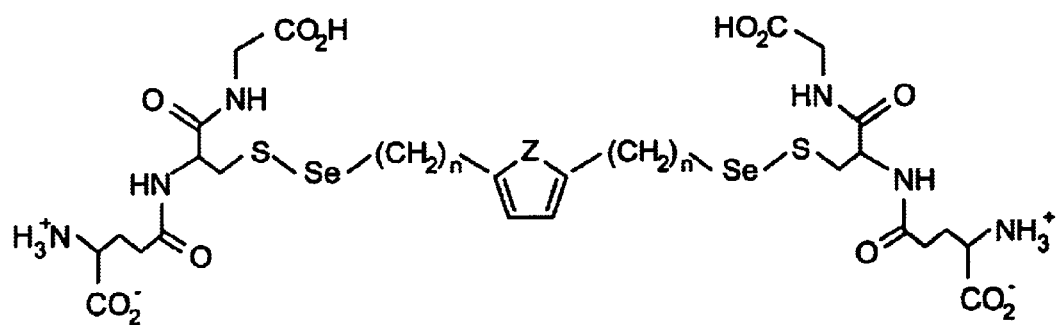
Figure 4:
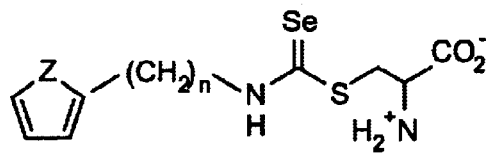
FIG. 4 illustrates general structures of cysteine and glutathione conjugates of isoselenocyanates of monosubstituted and disubstituted heterocyclic compounds: (a) monosubstituted cysteine conjugate; (b) disubstituted cysteine conjugate; (c) monosubstituted glutathione conjugate; and (d) disubstituted glutathione conjugate.
Figure 4:
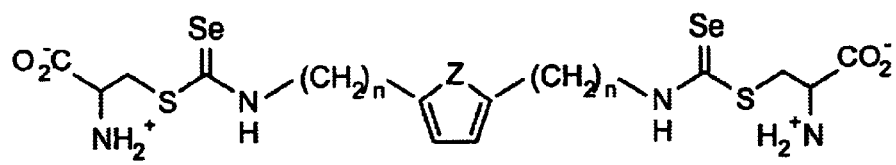
Figure 4:
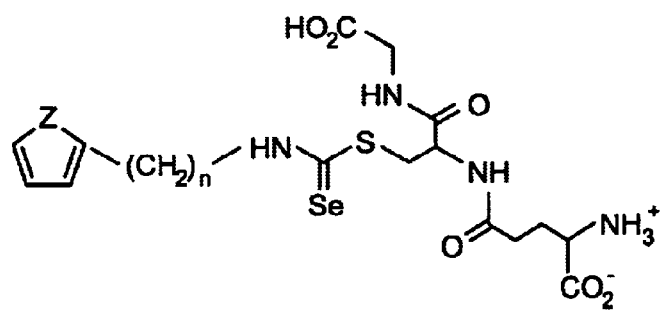
Figure 4:
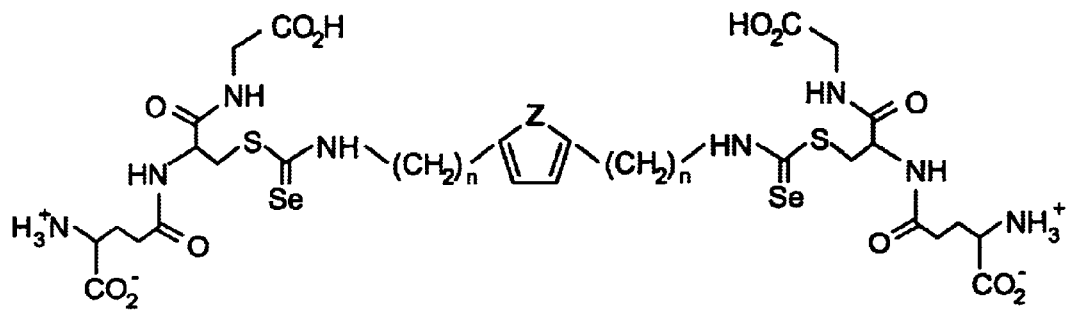

Conjugation of the cysteine or cysteine-containing peptide to the selenocyanate group or isoselenocyanate group of the compounds of the invention results in a —Se—S— linkage or a —NC(Se)—S— linkage, respectively, as illustrated in FIG. 2. Conjugates thus formed from the covalent linkage of cysteine, derivatized cysteine, or a cysteine-containing peptide to a selenocyanate group or an isoselenocyanate group of the compounds of formula I, II, or III, via the sulfur of the cysteine residue are collectively referred to herein as cysteine-containing conjugates of the compounds of formula I, II or III. Examples of cysteine and glutathione conjugates (monosubstituted and disubstituted) of selenocyanates and isoselenocyanates according to formula I and II are shown in FIGS. 3 and 4, respectively.

The present invention also provides methods for making the compounds of the invention, as generally described in Examples below.

The present invention also provides a chemopreventive composition that includes a compound of the invention and, optionally, a pharmaceutically acceptable carrier. The chemopreventive compounds of the present invention are formulated in pharmaceutical compositions and then, in accordance with the method of the invention, administered to a mammal, such as a human patient, in a variety of forms adapted to the chosen route of administration. The formulations include those suitable for oral, rectal, vaginal, topical, nasal, ophthalmic or parental (including subcutaneous, intramuscular, intraperitoneal and intravenous) administration.

The formulations may be conveniently presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into the desired formulations.

Formulations of the present invention suitable for oral administration may be presented as discrete units such as tablets, troches, capsules, lozenges, wafers, or cachets, each containing a predetermined amount of the chemopreventive compound as a powder or granules, as liposomes containing the chemopreventive agent, or as a solution or suspension in an aqueous liquor or non-aqueous liquid such as a syrup, an elixir, an emulsion or a draught. Such compositions and preparations should contain at least about 0.001% active compound. The percentage of the compositions and preparations may be varied and may conveniently be between about 0.001% to about 10% of the weight of a given unit dosage form. The amount of chemopreventive compound in such therapeutically useful compositions is such that the dosage level will be effective to prevent or suppress the development of cancer in the subject, for example by stimulating the production of phase II enzymes in the subject.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl-or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The chemopreventive compound may be incorporated into sustained-release preparations and devices.

The chemopreventive compounds of the invention can be incorporated directly into the food of the mammal's diet, as an additive, supplement, or the like. Thus, the invention further provides a food product containing a chemopreventive compound of the invention. Any food is suitable for this purpose, although processed foods already in use as sources of nutritional supplementation or fortification, such as breads, cereals, milk, and the like, may be more convenient to use for this purpose.

Formulations suitable for parenteral administration conveniently comprise a sterile aqueous preparation of the chemopreventive compound, or dispersions of sterile powders comprising the chemopreventive compound, which are preferably isotonic with the blood of the recipient. Isotonic agents that can be included in the liquid preparation include sugars, buffers, and sodium chloride. Solutions of the chemopreventive compound can be prepared in water, optionally mixed with a nontoxic surfactant. Dispersions of the chemopreventive compound can be prepared in water, ethanol, a polyol (such as glycerol, propylene glycol, liquid polyethylene glycols, and the like), vegetable oils, glycerol esters, and mixtures thereof. The ultimate dosage form is sterile, fluid and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the chemopreventive compound, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the chemopreventive compounds over a prolonged period can be achieved by including agents for delaying, for example, aluminum monostearate and gelatin.

Nasal spray formulations comprise purified aqueous solutions of the chemopreventive compound with preservative agents and isotonic agents. Such formulations are preferably adjusted to a pH and isotonic state compatible with the nasal mucous membranes.

Formulations for rectal or vaginal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the chemopreventive compound dissolved or suspended in one or more media such as mineral oil, petroleum, polyhydroxy alcohols or other bases used for topical pharmaceutical formulations. The compound of the invention is particularly suited to incorporation in a cosmetic lotion, créme, or sunscreen for use on the skin.

In addition to the aforementioned ingredients, the formulations of this invention may further include one or more accessory ingredients including diluents, buffers, binders, disintegrants, surface active agents, thickeners, lubricants, preservatives (including antioxidants) and the like.

Useful dosages of the compounds of formula I, II, or III, or cysteine-containing conjugates thereof, can be determined by comparing their in vitro activity and the in vivo activity in animals models. Methods for extrapolation of effective dosages in mice, and other animals, to humans are known in the art; for example, see U.S. Pat. No. 4,938,949, which is incorporated herein by reference, in its entirety.

Generally the concentration of the compound of formula I, II, or III, or cysteine-containing conjugates thereof, in a liquid composition, such as a topical lotion, will be about 0.001 wt-% to about 2.5 wt-%, preferably about 0.05 wt-% to about 1.0 wt-% (wt-%, weight percent, means grams of compound per 100 mL liquid). For adult humans, single dosages for injection, infusion, or ingestion will generally vary between about 1 mcg-500 mcg (mcg=microgram), and may be administered, for example about 1 to about 3 times per day, to yield levels of about 0.1 mcg to about 100 mcg per kg of body weight per day. Suitable doses to be administered are, in general, those which are sufficient to produce a chemopreventive effect, such as by inducing a demonstrable increase of phase II enzyme expression. This will typically not exceed 50 micromoles per kg of body weight per day, and may be much lower.

The invention further includes a method of protecting a mammal against the occurrence or progression of a cancer or a precancerous condition comprising administering to a mammal the chemopreventive composition of the invention in an amount effective to produce a cancer preventative effect. A cancer preventative effect includes both prevention of an initial occurrence of cancer (carcinogenesis) or a precancerous condition as well as the prevention of a metastasis of an existing cancer; it also includes slowing, halting, or reversing the progression of an existing cancer or precancerous condition. Accordingly, the chemopreventive composition can be administered as a therapeutic to treat an existing condition or as a prophylactic before, during or after possible or actual exposure to a known or suspected carcinogenic or procarcinogenic compound, event, or agent of any type.

A carcinogenic or procarcinogenic compound, event or agent is to be understood to include any mutagenic or potentially mutagenic agent, event, or condition including a mutagenic chemical compound, such as a toxicant; radioactivity, including but not limited to alpha, beta, or gamma emissions from an radioisotope; electromagnetic radiation of any wavelength or frequency, such as x-ray, ultraviolet, or infrared radiation; exposure to a magnetic field or an electromagnetic field (EMF), and the like.

Preferably, the chemopreventive compound of the invention is administered prophylactically before, during or after possible or actual exposure to a mutagenic chemical compound.

The objects, features and advantages of the present invention illustrated in the following examples, which incorporate particular materials and amounts, should not be construed to unduly limit this invention.

EXAMPLES

Example 1

Synthesis of Thienyl-2,5-di-methyleneselenocyanate (TDMSC)

Scheme 1

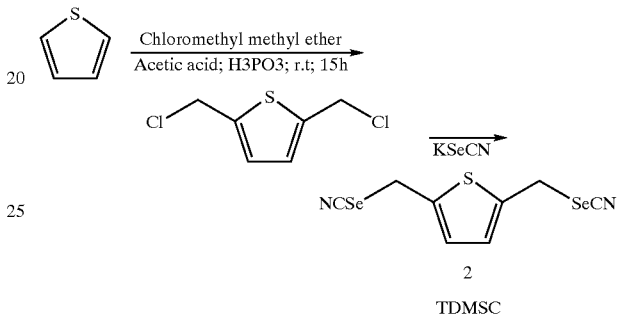

TDMSC

The starting compounds, thiophene, chloromethylether, acetic acid, and phosphoric acid, were purchased from Aldrich Chemical Company (Milwaukee, Wis.). The intermediate 2,5-thienylbis(methylene)chloride was synthesized by stirring thiophene (0.24 mol) with chloromethyl methyl ether (0.65 mol), in acetic acid (140 ml) in the presence of phosphoric acid (25 ml) at room temperature for 15 hours. The reaction mixture was poured into (500 ml) ice-water, and the product was extracted with diethyl ether. The ether layer was washed with water and dried with anhydrous magnesium sulfate. The solvent was removed under reduced pressure and the product was used in the next step without further purification. TDMSC 2 was prepared by modification of the procedure of El-Bayoumy et al., *Cancer Res.* 52:2402–2407 (1992). To a suspension of KSeCN in dry acetone stirred under nitrogen atmosphere, a solution of 2,5-thienylbis(methylene)chloride in dry, nitrogen flushed acetone was added slowly. After the completion of the reaction, the solvent was removed and the product was extracted with dichloromethane. After recrystallization, the compound purity was assessed by $^1$H NMR, and CI-MS. See data in Table 1.

Example 2

Synthesis of 2-Thienylmethyleneselenocyanate (TDMSC)

Scheme 2

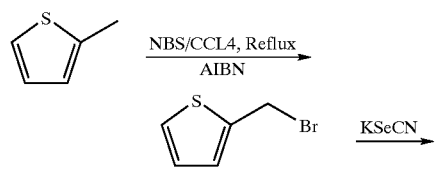

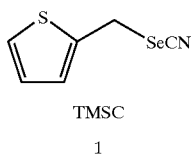

TMSC
1

Methylthiophene was purchased from Aldrich Chemical Co., (Milwaukee, Wis.). The starting compound 2-bromomethylthiophene was prepared as described in Pampalone et al., *Org. Pre. and Procedures* 1:209–212 (1969). A mixture of methylthiophene and N-bromosuccinamide in carbon tetrachloride, in the presence of 2,2'-azobisisobytyronitrile as a catalyst was refluxed for 3 h, under nitrogen atmosphere. After workup, 2-bromothiophene was purified by distillation under reduced pressure. TMSC 1 was synthesized by following the procedure used for TDMSC 2 described above. The purity and structures of the intermediate and final compounds were confirmed by $^1$H NMR and CI-MS. See data in Table 1.

Example 3

Synthesis of Selenophenyl-2,5-dimethyleneselenocyanate (SDMSC)

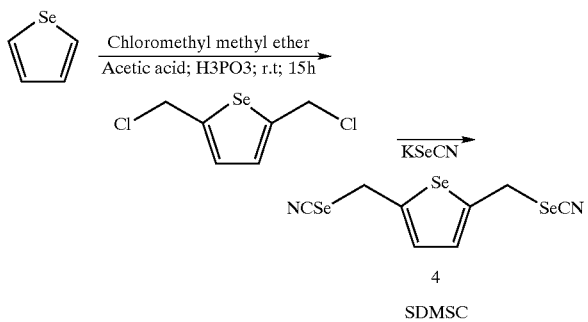

4
SDMSC

The starting compounds, selenophene, chloromethyl ether, acetic acid, and phosphoric acid, were purchased from Aldrich Chemical Company (Milwaukee, Wis.). The intermediate, 2,5-selenophenylbis(methylene)chloride was synthesized by stirring selenophene (0.24 mol) with chloromethyl methyl ether (0.65 mol) in acetic acid (140 ml) in the presence of phosphoric acid (25 ml) at room temperature for 15 hours. The reaction mixture was poured into (500 ml) ice-water, and the product was extracted with diethyl ether. The ether layer was washed with water and dried with anhydrous magnesium sulfate. The solvent was removed under reduced pressure and the product was used in the next step without purification.

The procedure used to make SDMSC 4 was similar to that used to synthesize TDMSC from 2,5-thienylbis(methylene) chloride described above in Example 1. The purity of the intermediate and the final product was confirmed by $^1$H NMR and CI-MS. See data in Table 1.

Example 4

Synthesis of Selenophenyl Methylene Selenocyanate (SMSC)

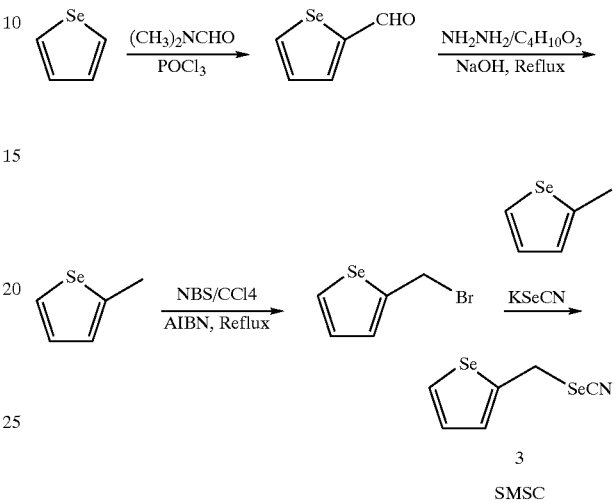

3
SMSC

Synthesis of Selenophene-2-Aldehyde.

Selenophene, phosphorous oxychloride, and dimethyl formamide were purchased from Aldrich Chemical Co., (Milwaukee, Wis.). Selenophene-2-aldehyde was prepared as described previously in Yuryev et al., *J. Gen. Chm* (USSR), 27:201–204 (1957). To a mixture of selenophene and dimethyl formamide, phosphorous oxychloride was added and heated for 1 hour at 65° C. After cooling it was transferred into a beaker containing crushed ice. Sodium acetate was added, and it was heated to boil, cooled, and extracted with ether. The crude product was purified by vacuum distillation.

Synthesis of 2-methylselenophene.

Hydrazine hydrate and diethylene glycol was purchased form Aldrich Chemical Co., (Milwaukee, Wis.). 2-methyleneselenophene was prepared by the reduction of selenophene-2-carboxaldehyde as described in Yuryev et al., *J. Gen. Chm* (USSR) 27:3193–3197 (1957). Crushed sodium hydroxide was added to a solution of selenophene-2-carboxaldehyde and hydrazine hydrate in diethylene glycol. The mixture was heated in an oil bath at 170–180° C. for 30–40 minutes. The fraction distilling up to 140° C. was collected, washed with 10% hydrochloric acid, followed by water, dried over calcium chloride, and was purified by distillation.

Synthesis of 2-Bromomethylselenophene.

The starting compound 2-bromomethylselenophene was synthesized by modification of the procedure used for the synthesis of 2-bromomethylthiophene described in Example 2. After purification, 2-bromomethylselenophene was converted into SMSC 3 as in Example 2 above for TMSC 1. The purity of the intermediate and final compound was assessed by $^1$H NMR and Cl-MS. See data in Table 1.

magnesium sulfate, and the solvent was removed under reduced pressure. The crude product was purified by column chromatography. The pure compound was characterized by spectroscopic analysis. Isoselenocyanate can be distinguished from the corresponding selenocyantate by a strong and wide I.R. band around 2100–2160 cm$^{-1}$, higher HPLC retention times, and higher δ values for CH$_2$—NSe) protons. The physical properties of the compounds are summarized in Table 1.

TABLE 1

Selenocyanates and Isoselenocyanates of thiophene and selenophene.

| Product | | | Yield | | I.R. (KBr) | | $^1$H-N.M.R (CDCl$_3$/TMS) |
|---|---|---|---|---|---|---|---|
| No. | Z | R$_1$ | R$_2$ | [%] | m.p. | RT$^a$ ν[cm$^{-1}$] | δ[ppm] |
| 1. | S | H | CH$_2$SeCN | 88 | 48–50° | 6.74 2146; 1417; 1249; 1206 1179; 1104; 1035; 859; 608 | 4.57(s, 2H, CH$_2$); 7.92(d, 1Har) 7.18(d, 1Har); 6.9(t, 1Har) |
| 2. | S | CH$_2$SeCN | CH$_2$SeCN | 85 | 120° | 3.68 2147; 1418; 1248; 1194; 1178 1095; 1022; 837; 815; 609 | 4.478(s, 4H, CH$_2$); 6.987(s, 2Har) |
| 3. | Se | H | CH$_2$SeCN | 40 | 54–56° | 9.20 2144; 1447; 1417; 1208; 1179 1104; 1035; 916; 795; 608 | 4.53(s, 2H, CH$_2$); 7.27(1Har):7.09(1Har); 6.9(1Har) |
| 4. | Se | CH$_2$SeCN | CH$_2$SeCN | 65 | 130–132° | 3.75 2146; 1774; 1625; 1475; 1413; 1245; 1194; 1175; 1100; 1007; 832; 814; 721; 603 | 4.55(s, 4H, CH$_2$); 7.12(s, 2Har) |
| 5 | S | H | CH$_2$NCSe | 35 | | 15.21 2126; 1721; 1461; 1435; 1364; 1331 1276; 1216; 1126; 1073; 1040; 852; 744; 704; 539 | 4.9(s, 2H, CH$_2$); 7.7(1Har); 7.02(1Har) 6.9(1Har) |
| 6. | S | CH$_2$NCSe | CH$_2$NCSe | 30 | 67–69° | 18.93 2146; 1967; 1634; 1428; 1325; 1202; 1150; 815; 642; 591 | 4.9(s, 4H, CH$_2$); 6.95(s, 2Har) |
| 7. | Se | CH$_2$NCSe | CH$_2$NCSe | 25 | 75–76° | 20.08 2146; 1635; 1558; 1488; 1322; 1266; 1205; 1138; 1035; 313; 733; 577 | 4.97(s, 4H, CH$_2$); 7.11(s, 2Har) |

$^a$The purity was >98% by HPLC. The analysis was done by running isocratic run of the solvent [methanol:water: formic acid: 60.40:01] at a flow rate of 1 ml/min, using MICROSORB C18 reverse-phase column. The CI-MS obtained were consistent with the structures.

Example 5

Synthesis of Thiophene and Selenophenyl Methylene Isoselenocyanates

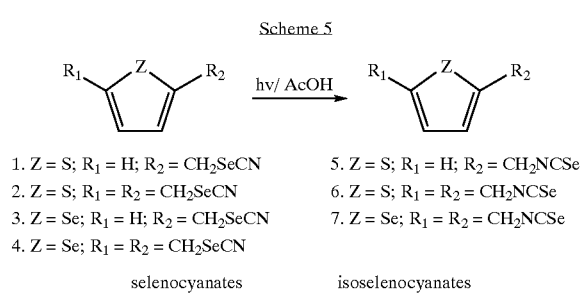

Scheme 5

1. Z = S; R$_1$ = H; R$_2$ = CH$_2$SeCN
2. Z = S; R$_1$ = R$_2$ = CH$_2$SeCN
3. Z = Se; R$_1$ = H; R$_2$ = CH$_2$SeCN
4. Z = Se; R$_1$ = R$_2$ = CH$_2$SeCN

5. Z = S; R$_1$ = H; R$_2$ = CH$_2$NCSe
6. Z = S; R$_1$ = R$_2$ = CH$_2$NCSe
7. Z = Se; R$_1$ = R$_2$ = CH$_2$NCSe selenocyanates → isoselenocyanates The isoselenocyanates were prepared by photochemical isomerization of the corresponding selenocyanate in dry acetic acid by a modification of the Suzuki procedure *Synthesis* 9:705–707 (1979). A 1 mmolar solution of the corresponding selenocyanate (1-4) was irradiated in dry acetic acid with a high pressure mercury lamp for 30–40 minutes. The mixture was diluted with water, the product was extracted with ether, the ether extract was washed with water and saturated sodium chloride, dried with anhydrous Example 6

Synthesis of 2-Thienylmethylene Selenocyanate Conjugate (TMSC-GSH)

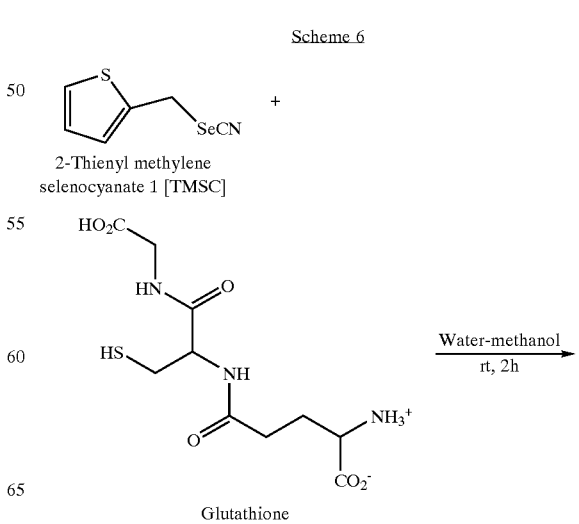

Scheme 6

2-Thienyl methylene selenocyanate 1 [TMSC]

Glutathione

Water-methanol rt, 2h

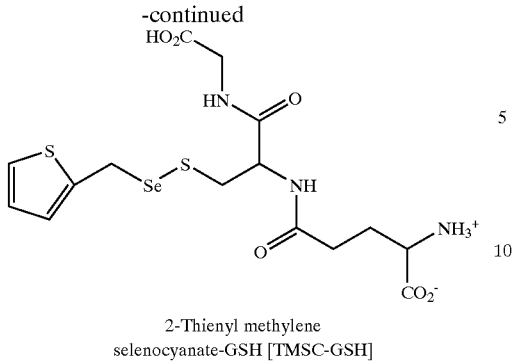

2-Thienyl methylene
selenocyanate-GSH [TMSC-GSH]
9

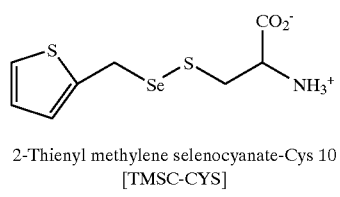

2-Thienyl methylene selenocyanate-Cys 10
[TMSC-CYS]

The 2-thienylmethylene selenocyanate-cysteine conjugate 10 (TMSC-Cys) was made and characterized using the procedure described in Example 6. In brief, a solution of cysteine (1 g, 8.3 mmol) in water (50 ml) and methanol (100 ml), was added a solution of 2-thienylmethylene selenocyanate (TMSC) (1 g, 4.9 mmol). Concentrated HCl (0.85 ml) was slowly added and stirred at room temperature for I hour. The solution was concentrated, and the light yellow color solid was washed with cold methylenechloride, acetonitrile, to remove any traces of unreacted TMSC and side products such as diselenide and water. The solid was dried under vacuum and characterized as above.

The 2-thienylmethylene selenocyanate-glutathione conjugate 9 (TMSC-GSH) was synthesized by modifying the procedure of Kawamori et al., *Int. J. Oncol.* 13:29–34 (1999). To a solution of glutathione (2.2 g, 7.15 mmol) in water (50 ml) and methanol (100 ml), was added to solution of 2-thienylmethylene selencyanate (TMSC) (1 g, 4.9 mmol). Concentrated HCl (0.85 ml) was slowly added and stirred at room temperature for 1 hour. The sodium was concentrated, the white precipitate was washed with cold methylenechloride, acetonitrile, to remove any traces of unreacted TMSC and side products such as diselenide. The white solid was washed with acidic water to remove traces of glutathione. The solid was dried under vacuum and the identity of the compound was confirmed by HNMR: (DMSO-$d_{6, 300}$ MHz) $\delta$1.58–2.2 (2H, m) $\delta$2.3 (2H, m) $\delta$2.9 (1H,m), $\delta$3.4(1H, t), $\delta$3.5(1H, t), $\delta$3.7 (2H, t) $\delta$4.4 (1H, m), $\delta$4.2(2H, s), $\delta$6.75–7.24 (2H, m), $\delta$7.24–7.64 (1H, m) $\delta$8.28–8.94(2H, m). The $\delta$ values of benzylselenocyanate-glutathione conjugates were used as reference. Kawamori et al., *Int. J. Oncol.* 13:29–34 (1999). Electrospray ionization mass spectra in methanol (from a stock of DMSO-$d_6$) by infusion method was done. Nine isotopic mass ion peaks were observed and that were identifcal witht he theoretical mass peaks obtained by formula simulation. 479.9, 480.9, 481.9, 482.9, 483.9, 484.9, 485.9, 486.9, 487.8. The HPLC purity of the compound was >99%.

Example 7

Synthesis of 2-Thienylmethylene Selenocyanate-cysteine Conjugate (TMSC-Cys)

Scheme 7

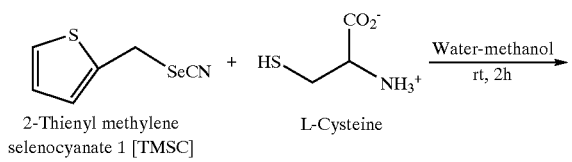

Example 8

Glutathione S-Transferase Assay

The activity of cytosolic was assayed according to the method of Habig et al. using 1-chloro-2,4-dinitrobenzene (CDNB) as the substrate Habig et al, *J. Biol. Chem.* 249:7130–7139 (1974). The complete solution contains, in a total volume of 2.0 mL, 0.1 M phosphate buffer, pH 6.5, 5 mM glutathione, 1 mM CDNB, and 20 $\mu$L of the cytosol. The reaction was monitored at 340 nm in a Beckman Model DU65 UV-VIS spectrophotometer. Assays were performed at 30° C. Complete assay mixture without the cytosolic enzyme was used as the reference blank. Data as analyzed by the Student's "t" test and P values were obtained in comparison to the control. A compound that has greater than 40% and 80% GST increase in the liver and small bowel mucosa (SBM), respectively, over the control level is generally regarded as worth further investigation.

The influence of selenocyanates, isoselenocyanates of thiophene and selenophene and the reference compound (p-XSC) on GST activity in five different tissues of A/J mice are summarized in Tables 2 and 3.

TABLE 2

Effects of Selenocyanates and Isoselenocyanates of Thiophene and Selenophene on the Activity of Glutathione S-Transferase in the Tissue of Female A/J Mice.

| Compound | Dose[a] | Small intestinal Mucosa GST act.[b] | Ratio Test/con | Liver GST act.[b] | Ratio Test/con | Forestomach GST act.[b] | Ratio Test/con | Lung GST act.[b] | Ratio Test/con | colon GST act.[b] | Ratio Test/con |
|---|---|---|---|---|---|---|---|---|---|---|---|
| Control |  | 0.34 ± 0.03 |  | 1.13 ± 0.08 |  | 0.78 ± 0.04 |  | 0.47 ± 0.11 |  | 0.40 ± 0.04 |  |
| (1) TMSC | 0.04 | 0.42 ± 0.12 | 1.24 | 1.20 ± 0.3[e] | 1.94 | 1.46 ± 0.33[f] | 1.87 | 0.63 ± 0.13[c] | 1.34 | 0.41 ± 0.05 | 1.03 |
| (1) TMSC | 0.02 | 0.39 ± 0.1 | 1.15 | 1.49 ± 0.14[e] | 1.32 | 1.13 ± 0.26[g] | 1.45 | 0.59 ± 0.04[g] | 1.26 | 0.43 ± 0.03 | 1.08 |
| (5) TMISC | 0.04 | 0.47 ± 0.07[g] | 1.38 | 2.67 ± 0.3[c] | 2.36 | 1.32 ± 0.21[e] | 1.69 | 0.73 ± 0.06 | 1.55 | 0.43 ± 0.02 | 1.08 |
| (5) TMISC | 0.02 | 0.42 ± 0.03[d] | 1.24 | 1.83 ± 0.32[f] | 1.62 | 1.10 ± 0.23[f] | 1.41 | 0.63 ± 0.08 | 1.34 | 0.43 ± 0.02 | 1.08 |
| (2) TDMSC | 0.04 | 0.40 ± 0.16 | 1.18 | 1.26 ± 0.21 | 1.12 | 0.90 ± 0.11[g] | 1.15 | 0.54 ± 0.09 | 1.15 | 0.40 ± 0.01 | 1.00 |
| (2) TDMSC | 0.02 | 0.35 ± 0.01 | 1.03 | 1.43 ± 0.2[g] | 1.27 | 0.90 ± 0.12 | 1.15 | 0.49 ± 0.07 | 1.04 | 0.40 ± 0.04 | 1.00 |
| (4) SDMSC | 0.04 | 0.36 ± 0.02 | 1.06 | 1.69 ± 0.18[e] | 1.50 | 0.94 ± 0.18 | 1.21 | 0.55 ± 0.07 | 1.17 | 0.44 ± 0.04 | 1.10 |
| (4) SDMSC | 0.02 | 0.34 ± 0.01 | 1.00 | 1.20 ± 0.11[g] | 1.06 | 1.05 ± 0.28 | 1.35 | 0.58 ± 0.08 | 1.23 | 0.45 ± 0.02[g] | 1.13 |

[a]mmol/Kg body weight, compounds administered by gavage as solution in 0.3 ml corn oil.
[b]GST activity ($\mu$mol/min mg protein) was determined according to the method of Habig et al. (1974) using CDNB as the substrate.
[c]P values compared with the control were obtained by the two-tailed student's t-test (n = 5); $P < 0.0005$.
[d]$P < 0.001$;
[e]$P < 0.005$;
[f]$P < 0.01$;
[g]$P < 0.05$.
TMSC; 2-Thienyl methyl selenocyanate (1); TMISC; 2-Thienyl methyl isoselenocyanate (5), TDMSC; Thienyl-2,5-di(methyl selenocyanate) (2), SDMSC; Selenophenyl-2,5-di(methyl selenocyanate) (4).

TABLE 3

Effects of Selenocyanates and Isoselenocyanates of Thiophene and Selenophene on the Activity of Glutathione S-Transferase in the Tissue of Female A/J Mice.

| Compound | Dose[a] | Small intestinal Mucosa GST act.[b] | Ratio Test/con | Liver GST act.[b] | Ratio Test/con | Forestomach GST act.[b] | Ratio Test/con | Lung GST act.[b] | Ratio Test/con | colon GST act.[b] | Ratio Test/con |
|---|---|---|---|---|---|---|---|---|---|---|---|
| Control |  | 0.22 ± 0.04 |  | 1.28 ± 0.17 |  | 1.11 ± 0.29 |  | 0.34 ± 0.02 |  | 0.65 ± 0.04 |  |
| (3) SMSC | 0.04 | 0.20 ± 0.02 | 0.91 | 2.02 ± 0.33[e] | 1.58 | 1.12 ± 0.19 | 1.01 | 0.34 ± 0.06 | 1.00 | 0.69 ± 0.09 | 1.06 |
| (3) SMSC | 0.02 | 0.19 ± 0.5 | 0.86 | 1.04 ± 0.18[g] | 0.81 | 0.89 ± 0.22 | 0.8 | 0.40 ± 0.03[f] | 1.18 | 0.70 ± 0.05 | 1.08 |
| (6) TDMISC | 0.04 | 0.53 ± 0.03[c] | 2.41 | 3.24 ± 0.39[e] | 2.53 | 1.23 ± 0.35 | 1.11 | 0.59 ± 0.29 | 1.73 | 0.74 ± 0.04[f] | 1.14 |
| (6) TDMISC | 0.02 | 0.54 ± 0.11[e] | 2.45 | 2.43 ± 0.46[e] | 1.90 | 1.03 ± 0.20 | 0.93 | 0.44 ± 0.04[f] | 1.29 | 0.73 ± 0.026[g] | 1.12 |
| (7) SDMISC | 0.04 | 0.62 ± 0.04[c] | 2.82 | 3.00 ± 0.13[c] | 2.34 | 1.27 ± 0.28 | 1.14 | 0.40 ± 0.04 | 1.16 | 0.87 ± 0.03[c] | 1.34 |
| (7) SDMISC | 0.02 | 0.50 ± 0.14[e] | 2.26 | 3.06 ± 0.41[e] | 2.39 | 1.22 ± 0.21 | 1.10 | 0.45 ± 0.04[f] | 1.31 | 0.80 ± 0.03[c] | 1.23 |
| p-XSC | 0.02 | 0.21 ± 0.06 | 0.95 | 1.64 ± 0.45 | 1.28 | 0.98 ± 0.27 | 0.88 | 0.48 ± 0.13 | 1.41 | 0.72 ± 0.07 | 1.10 |

[a]mmol/Kg body weight, compounds administered by gavage as solution in 0.3 ml corn oil.
[b]GST activity ($\mu$mol/min mg protein) was determined according to the method of Habig et al. (1974) using CDNB as the substrate.
[c]P values compared with the control were obtained by the two-tailed student's t-test (n = 5); $P < 0.0005$.
[d]$P < 0.001$;
[e]$P < 0.005$;
[f]$P < 0.01$;
[g]$P < 0.05$.
SMSC; 2-Selenophenyl methyl selenocyanate (3); TDMISC; Thienyl-2,5-di(methyl isoselenocyanate) (6), SDMISC; Selenophenyl-2,5-di(methyl isoselenocyanate) (7), p-XSC; p-Xyleneselenocyanate.

Surprisingly, an overall increase in GST activity was observed in all the tissues of treated mice in comparison with the control group and also in comparison with that of the reference compound p-XSC. The GST induction was significant in liver and in small intestine mucosa (SBM). Statistically significant, dose response induction was observed in the liver of mice treated with all test compounds except in the group treated with SMSC 3 (Table 2). The highest induction (T/C (test/control) =2.53; P<0.005) was observed in TDMISC 6 (Table 3). A greater than 2.3-fold increase in induction was observed in the TMISC 5 (high dose) (Table 2), SDMISC 7 (high dose), SDMISC 7 (low dose) groups (Table 3). In the SBM 2.83-fold induction (P<0.0005) was observed in the SDMISC 7 (high dose) treated group. TDMISC 6 (high dose), TDMISC 6 (low dose), and SDMISC 7 (low dose) showed a greater than 2.2-fold induction and the data was statistically significant (Table 3).

Significant dose response was observed in the forestomach and lung of the TMSC 1 (high dose) and TMSC 1(low dose) groups (Table 2). TMISC 5 (high dose) and TMISC 5 (low dose) treated groups showed dose response induction in the forestomach only (Table 2). In the colon, dose response induction was observed in the SDMISC (high dose) group, which was statistically significant (Table 3).

Example 9

Glutathione Concentrations

GSH was quantitated by modification of the procedure Siller-Cepeda et al. *Plant Cell Physiol.* 32:1179–1185 (1991). Aliquots of tissue homogenates were mixed with equal volumes of 20% PCA containing 2 mM BPDS. Vortex, centrifuge at 7800× g for 15 minutes at 4° C. and 250 μl supernatant transferred into a microfuge tube containing 25 μl of γ-glu—glu as internal standard. The samples were carboxymethylated with 25 μl of 100 mM iodoacetic acid dissolved in 0.2 mM m-cresol purple sodium salt solution. The pH of the solution was adjusted to 9–10 by adding 350 μi of KOH (2M)-KHCO$_3$ (2.4 M) mixture and incubated in the dark for 15 minutes. After carboxymethylation, the samples were derivatized with 500 μl of 1% dinitrofluorobenzene (DNFB) and kept in the dark at 4° C. overnight. The samples were centrifuged at 13,000× g for 15 minutes, filtered through 0.2 μm filter, and were analyzed with a SHIMADZU two-pump gradient HPLC system. Samples were injected by a SHIMADZU SIL-10AV Autoinjector onto a Varian 3-aminopropyl MICROSORB-MV column (4.6×250 mm) operated at ambient temperaure with a flow rate of 1 ml/min. Absorbance of the dinitrophenyl derivatives was monitored at 365 nm. The amount of GSH was calculated from a standard curve using γ-glu—glu as internal standard.

Effects of the test compounds and the model compound on the concentration of GSH in the liver and small intestinal mucosa of female A/J mice are summarized in Table 4. The liver GSH level was increased (T/C=1.7; P<0.05), (T/C=1.56; P<0.05), (T/C=1.46; P<0.005), and (T/C=1.38; P<0.05) in TMSC 1 (high dose), TMISC 5 (high dose), TMISC 5 (low dose), and SMSC 3 (high dose) respectively. In the SBM an increase in induction from 1.90 to 1.36 was observed and the data was found to be statistically significant.

Example 10

UDP-Glucuronosyltransferase (UDP-GT) Activity

Microsomal samples were assayed for enzymatic conjugation by modifying the procedure of Zakim et al., *Methods of Biochemical Analysis*, ed. David Glick, 21:1–37, (1973). using o-aminophenol as the substrate. The complete assay solution contains, in a total volume of 500 μl, 0.25 M phosphate buffer (pH 7.6), 0.002 M o-aminophenol, 0.05 M UDPGA, 0.125 M magnesium chloride and 100 III microsomes. The mixture was incubated for 30 minutes. Reactions were stopped by the addition of 500 μl of TCA-sodium phosphate reagent. The precipitated protein was removed, 100 μl of 0.05% sodium nitrite was added to 950 μl of the supernatant solution and allowed to stand for 5 minutes. 100 μl of 0.5% ammonium sulfamate was added, after 5 minutes. 100 μl of 0.12% N-(-1-naphthyl) ethylenediamine dihydrochloride was added and incubated for 2 hours in the dark; and the difference in the optical density between the blanks and the samples were recorded at 555 nm in a Beckman model DU65 UV-VIS spectrophotometer. The UDP-GT activity was calculated using the extinction coefficient 29 mM-1 cm-1 for the coupled product.

The results of the investigation are summarized in Table 5. A 3.33-fold increase in enzyme activity, compared to the control group (P<0.05) was observed in the groups treated with TMISC 5 (low dose). An increase in enzyme activity (T/C=3.0; P<0.005), (T/C=2.33; P<0.05; P<0.05) and (T/C=2.67; P<2.67) was observed in TMSC 1 (low dose), TMISC 5 (high dose), TDMSC 2 (high dose), and SDMSC 4 (low dose) treated groups respectively.

TABLE 4

Effects of Selenocyanates and Isoselenocyanates of Thiophene and Selenophene on the Concentrtion of GSH in the Tissue of Female A/J Mice.

| | Liver | | | Small intestinal Mucosa | | | Liver | |
|---|---|---|---|---|---|---|---|---|
| Compound | Dose[a] | GSH conc.[b] | Ratio Test/con | Compound | GSH conc.[b][b] | Ratio Test/con | GSH conc.[b] | Ratio Test/con |
| Control | | 3.85 ± 1.79 | | Control | 2.11 ± 0.58 | | 3.55 ± 1.02 | |
| (1) TMSC | 0.04 | 5.99 ± 1.68[c] | 1.56 | (3) SMSC | 2.11 ± 0.39 | 1.00 | 4.89 ± 0.57[c] | 1.38 |
| (1) TMSC | 0.02 | 5.05 ± 1.41 | 1.31 | (3) SMSC | 1.88 ± 0.4 | 0.89 | 3.49 ± 0.90 | 0.98 |
| (5) TMISC | 0.04 | 6.56 ± 1.05[c] | 1.70 | (6) TDMISC | 3.71 ± 0.31[d] | 1.76 | 5.29 ± 1.09 | 1.49 |
| (5) TMISC | 0.02 | 5.63 ± 1.01[d] | 1.46 | (6) TDMISC | 2.26 ± 1.87 | 1.07 | 3.38 ± 1.11 | 0.95 |
| (2) TDMSC | 0.04 | 4.60 ± 2.13 | 1.20 | (7) SDMISC | 4.00 ± 0.35[d] | 1.90 | 4.25 ± 1.02 | 1.20 |
| (2) TDMSC | 0.02 | 4.91 ± 1.16 | 1.28 | (7) SDMISC | 2.86 ± 0.14[c] | 1.36 | 4.63 ± 1.30 | 1.30 |
| (4) SDMSC | 0.04 | 5.34 ± 1.36 | 1.39 | p-XSC | 1.93 ± 0.54 | 0.91 | 3.50 ± 0.75 | 0.99 |
| (4) SDMSC | 0.02 | 3.58 ± 1.86 | 0.93 | | | | | |

[a]mmol/Kg body weight, compounds were administered by gavage as solution in 0.3 ml corn oil..
[b]GSH concentration (μmol/gm tissue weight) was determined by High Performance Liquid Chromatography according to Reed et al. (1980).
[c]P values compared with the control were obtained by the two-tailed student's t-test (n = 5); P < 0.05.
[d]P < 0.005;
TMSC; 2-Thienyl methyl selenocyanate (1); TMISC; 2-Thienyl methyl isoselenocyanate (5), TDMSC; Thienyl-2,5-di(methyl selenocyanate) (2), SDMSC; Selenophenyl-2,5-di(methyl selenocyanate) (4), SMSC; 2-Selenophenyl methyl-selenocyanate (3); TDMISC; Thienyl-2,5-di (methyl isoselenocyanate) (6), SDMISC; Selenophenyl-2,5-di(methyl isoselenocyanate) (7), p-XSC; p-Xyleneselenocyanate

TABLE 5

Effects of Selenocyanates and Isoselenocyanates of Thiophene and Selenophene on the on the Activity of UDP-GT in the Tissue of Female A/J Mice.

| | | Liver | | | | Liver | |
|---|---|---|---|---|---|---|---|
| Compound | Dose[a] | GSH conc.[b] | Ratio Test/con | Compound | Dose | GSH conc.[b] | Ratio Test/con |
| Control | | 4.43 ± 1.29 | | Control | | 4.05 ± 0.82 | |
| (1) TMSC | 0.04 | 12.41 ± 3.06[d] | 2.80 | (3) SMSC | 0.04 | 9.56 ± 4.23[d] | 2.36 |
| (1) TMSC | 0.02 | 10.84 ± 1.57[c] | 2.45 | (3) SMSC | 0.02 | 6.15 ± 1.20[d] | 1.52 |
| (5) TMISC | 0.04 | 9.66 ± 2.49 | 2.18 | (6) TDMISC | 0.04 | 7.98 ± 2.49 | 1.49 |
| (5) TMISC | 0.02 | 8.31 ± 1.92[c] | 1.88 | (6) TDMISC | 0.02 | 6.08 ± 0.76[d] | 1.50 |
| (2) TDMSC | 0.04 | 12.44 ± 2.31[c] | 2.81 | (7) SDMSC | 0.04 | 6.46 ± 1.95 | 1.60 |
| (2) TDMSC | 0.02 | 7.00 ± 1.07[c] | 1.58 | (7) SDMSC | 0.02 | 10.37 ± 1.99[d] | 2.56 |
| (4) SDMSC | 0.04 | 10.75 ± 2.04[d] | 2.43 | p-XSC | 0.04 | 7.60 ± 2.47[d] | 1.88 |
| (4) SDMSC | 0.02 | 10.17 ± 2.37[c] | 2.30 | | 0.02 | | |

[a]mmol/Kg body weight, compounds administered by gavage as solution in 0.3 ml corn oil.
[b]UDP-GT activity (nmol/min/mg protein) was determined according to the method of Zakim et al. (1973) using o-aminiphenol as the substrate.
[c]P values compared with the control were obtained by the two-tailed student's t-test (n = 5); $P < 0.05$;
[d]$P < 0.005$;
TMSC; 2-Thienyl methyl selenocyanate (1); TMISC; 2-Thienyl methyl isoselenocyanate (5), TDMSC; Thienyl-2,5-di(methyl selenocyanate) (2), SDMSC; Selenophenyl-2,5-(di-methyl selenocyanate) (4), SMSC; 2-Selenophenyl methyl-selenocyanate (3); TDMISC; Thienyl-2, 5-di(methyl isoselenocyanate) (6), SDMISC; Selenophenyl-2,5-di(methyl isoselenocyanate) (7), p-XSC; p-Xyleneselenocyanate

Example 11

Inhibition of Aberrant Crypt (AC) Formation

Precancerous lesions called aberrant crypts (AC) are used as a marker for colon carcinogenesis. Mice and rats, when exposed to colon-specific carcinogen, develop preneoplastic changes in colon crypts which leads to malignancy through dysplasia-carcinoma sequence. It is well established that colon-specific carcinogens induce AC while non-toxic chemicals do not. McLellan et al., *Cancer Res.* 48:6183–6186 (1988); McLellan et al., *Cancer Res.* 48:2311–2315 (1988).

The effect of colon-specific carcinogenesis is typically seen in the induction of AC formation in less than two weeks. AC formation is dose dependent and can be quantitated without elaborate instrumentation. In view of the short time-frame required to get quantifiable results, this bio-assay is a useful prescreening tool for the evaluation of chemopreventative efficacy of compounds that are effective against colon cancer. The protocol for aberrant crypts is shown below:

| Group | Dose mmol/kg body weight | # Animals | Inhibitor | DMH | Inhibitor |
|---|---|---|---|---|---|
| VCON | | 5 | – | – | – |
| TDMSCH | 0.04 | 5 | + | – | + |
| TMISCH | 0.04 | 5 | + | – | + |
| DMH | | 12 | – | + | – |
| TDMSCL/DMH | 0.03/DMH | 12 | + | + | + |
| TMISCL/DMH | 0.03/DMH | 12 | + | + | + |

Female $CF_1$ mice, 3 weeks of age, were purchased from Harlan Sprague-Dawley, Indianapolis, Ind. They were housed, 5 mice per cage, in temperature and humidity-controlled animal quarters with 12 hours light/dark cycle and fed AIN 76A semipurified diet until the ent of the experiment. Water was given ad libitum. The animals were separated into experimental and control groups. The test compounds 0.03–0.04 mmol/kg body weight dissolved in 0.3 µl corn oil, were given by gavage one per day for 8 days. One hour after the inhibitors administration on the $4^{th}$ and $8^{th}$ days, 0.4 mg of DMH in 0.2 mL of 0.001 M EDTA, adjusted to pH 6.5 with sodium bicarbonate, was given by gavage. Starting on the $9^{th}$ day, the inhibitors were given once every other day for an additional 3 weeks. This regimen of inhibitor administration ensures the coverage both the initiation and post initiation periods of carcinogen exposure.

At the end of the 3 week period, the animals were sacrificed and the colons removed. The starting and terminating weights of the animals were recorded. The procedures for the determination of aberrant crypts were those reported by Bird (*Cancer Letters* 37:147–151 (1987)). The mouse colon including the caecum was removed, rinsed with PBS, and opened longitudinally. The colon contents was removed by washing with PBS. The colon was spread mucosal side up on a piece of filter paper and fixed in buffered formalin overnight. It was then stained with 0.2% methylene blue in PBS for 60 min. The AC foci was read under light microscope. The AC are topographically distinguished by their increased size, increased pericryptal zone, and thicker and deeply stained epithelial lining compared to normal crypts. The number of foci and AC in the colorectal and caecal parts of the colon were recorded separately. The significance of the data was determined by the analysis of variance method. The significance of the incidence of aberrant crypts bearing animals was analyzed by the $\chi^2$ test. The aberrant crypts were examined histologically to verify the dysplastic nature of the changes in animals treated with carcinogens and those treated with carcinogens and inhibitors.

The data on the inhibition of the aberrant crypt formation by the test compounds is summarized in Table 6. No AC were found in the corn oil vehicle control groups. More than 70% protection was observed in mice treated with a low dose of TMISC 5. In a similar way, more than 50% protection was observed in mice treated with a low dose of TDMSC 2.

TABLE 6

The Inhibition of Aberrant Crypts Formation by Selenocyanates and Isoselenocyanates in Female CF1 Mice

| group # | 1 VCON | 2 TMISCH | 3 TDMISCH | 4 DMH | 5 TDMSCL/DMH | 6 TMISCL/DMH |
|---|---|---|---|---|---|---|
| # of animals[a] | 5 | 5 | 1 | 16 | 10 | 12 |
| Total ACF | 0 | 0 | 0 | 18 | 4 | 4 |
| Total AC | 0 | 0 | 0 | 23 | 4 | 4 |
| ACF/Colon | 0.00 | 0.00 | 0.00 | 1.13 | 0.50 | 0.33 |
| AC/Colon | 0.00 | 0.00 | 0.00 | 1.44 | 0.50 | 0.33 |
| AC/Foci | 0.00 | 0.00 | 0.00 | 1.28 | 1.00 | 1 |
| % animals[b] | 0.0 | 0.0 | 0.0 | 43.7 | 24.0 | 25.0 |

Female CF1 mice (from charies River laboratories), three weeks of age, shipped the week of January 31, 2000. 5 mice per cage. Determination of aberrant crypts: the colon was spread, mucosal side up, on a piece of paper, fixed in formalin and the AC foci were read under microscope blue after staining with 0.2% methylene.
TMSCH (high dose); TMSCL (low dose) TMISCH; 2-Thienyl methyl isoselenocyanate (high dose). TMISC; 2-Thienyl methyl isoselenocyanate, TDMSC; Thienyl-2,5-di(methyl selenocyanate), *DMISC; thienyl-2,5-di(methyl isoselenocyanate),
number of animals at sacrifice[a]

Example 12

Microsomal P450 Assay

The induction of the cytochrome P450-dependent monooxygenase enzyme system, by chemopreventative compounds, in a way which influences their ability to metabolize or detoxify chemical carcinogens is recognized as a major mechanism of chemoprevention. A typical protocol is given as follows:

| Groups | # Animals | Test compounds proposed |
|---|---|---|
| 1 | 5 | None-vehicle (cottonseed oil) only |
| 2 | 5 | SMSC 3 80% MTD |
| 3 | 5 | SMISC 8 80% MTD |
| 4 | 5 | SDMSC 4 80% MTD |
| 5 | 5 | SDMISC 7 80% MTD |
| 6 | 5 | TMSC 1 80% MTD |
| 7 | 5 | TMISC 5 80% MTD |
| 8 | 5 | TDMSC 2 80% MTD |
| 9 | 5 | TDMISC 6 80% MTD |

Female A/J mice from Charles River Laboratory (Boston, Mass.), 7 weeks old, will be fed a semipurified (AIN76A) diet from Tellad (Wis.) for one week prior to and throughout the entire duration of the experiment. Animals will be housed in temperature controlled animal quarters with a 12/12 h light dark cycle. Water will be given ad libitum. The animals will be cared for by trained animal technicians.

The procedures for the preparation of cytosolic and microsomal fractions from liver, lung, forestomach, and small and large bowel mucosa of laboratory animals will be essentially those described in Lam et al., *Nutr. Cancer* 12:43–47 (1989) and Guo et al., *Carcinogenesis* 13:2205–2210 (1992). The animals will be given 80% MTD of the test compounds in 0.3 ml cottonseed oil or other appropriate vehicle by gavage once every two days for a total of 3 doses. In general, five animals per group will be used. Each sample represents one individual animal. Twenty-four hours after the third administration, the animals will be sacrificed. The liver, lung, forestomach, and the mucosa from the proximal ⅓ of the small intestine and the entire length of the large intestines, including the caecum, will be removed. The tissues will be homogenized in cold homogenizing buffer (50 mM Tris-Cl, 1.15% KCl, pH 7.4), and the homogenates will be centrifuged at 9,000×g for 20 min to obtain the post-mitochondrial supernatant fraction. Cytosolic fractions will be collected after microsomes are pelleted by a subsequent centrifugation at 10,000× g for 60 min. Microsomes will be suspended in 50 mM potassium phosphate buffer, pH 7.4, after being washed once. Both microsomal and cytosolic samples will be stored in aliquots at −80° C. until required for the experiment. The protein concentration of these samples will be determined by the method of Lowry et al. (*J. Biol. Chem.* 193:265 (1951)).

The O-dealkylase activities of ethoxyresorufin (EROD) and pentoxyresorufin (PROD), which reflects the activities of P450s 2E 1 and 2B 1 respectively, will be assayed by the method of Guo et al. (*Carcinogenesis* 13:2205–2210 (1992)). Ethoxyrufin or pentoxyresorufin at 5 μM will be preincubated with microsomes at 37° C. for 2 min in the presence of 100 mM HEPES (pH 7.8), 1.6 mg BSA/ml and 5 mM $MgSO_4$ in a total volume of 1.0 ml. The reaction will be initiated by the addition of an NADPH-generating system and will be terminated by adding 2 ml methanol at intervals of 2.5, 5, and 10 min. The mixture will be centrifuged for 10 min after brief vortexing. Blanks will be prepared by incubation without the enzyme system. Fluorescence will be measured at Ex 550 and Em 585 nm. The enzyme activities will be calculated by comparing to a resorufin standard curve subjected to the same incubation procedures.

Example 13

DNA Methylation in the Mouse Lung

The organ-specific induction of lung tumors by NNK in all animal species, irrespective of the mode of administration, strongly supports its possible role in the development of lung cancer among smokers. Morse et al., *Cancer Res.* 49:549–553 (1989); Hecht et al., *Cancer Res.* 46:498–503 (1986); Hecht et al., *Carcinogenesis* 9:875–884 (1988); Hoffmann et al., *Cancer Res.* 45:935–944 (1985); Rivenson et al., *Cancer Res.* 48:6912–6917 (1988); and Morse et al., *Cancer Res.* 50:2613–2617 (1990). In the U.S. alone, more than 53 million people are directly affected by exposure to the risk of this carcinogen through cigarette smoking, and many more are indirectly affected by NNK polluted environment. Therefore, the evaluation of the efficacy of the test compounds in the inhibition of NNK-induced methylation will be of great importance.

The reactive intermediate, obtained as a result of NNK metabolic activation, methylates the guanine base of DNA. A reduction of $O^6$-methylguanine has been correlated with the inhibition of carcinogenesis in the lung of A/J mice by organoselenium compounds and other chemopreventative agents. Chung et al., *Carcinogenesis*, 6:539–543 (1985) and Tanaka et al., *Cancer Res.*, 57:3644–3648 (1997). The inhibition of NNK-induced DNA methylation in mice by test compounds will be performed according to the method of Chung et al. (*Carcinogenesis*, 6:539–543 (1985). A typical protocol is shown below:

| Groups | # Animals | Test compounds proposed | |
|---|---|---|---|
| 1 | 5 | None- vehicle only | |
| 2 | 6 | NNK (10 µmol) | |
| 3 | 6 | SMSC 3 | 80% MTD |
| 4 | 6 | SMISC 8 | 80% MTD |
| 5 | 6 | SDMSC 4 | 80% MTD |
| 6 | 6 | SDMISC 7 | 80% MTD |
| 7 | 6 | TMSC 1 | 80% MTD |
| 8 | 6 | TMISC 5 | 80% MTD |
| 9 | 6 | TDMSC 2 | 80% MTD |
| 10 | 6 | TDMISC 6 | 80% MTD |

Female A/J mice of 7 weeks of age will be obtained from Charles River Laboratory, Boston, Mass. The mice will be fed AIN-76A semipurified diet pellets. They will be grouped 3 to 5 per cage with hardwood bedding and maintained at 20 ±2° C., 50% relative humidity, and a 12 hours/12 hours light dark cycle. The animals will be given proper care and maintenance in accordance with the institutional guidelines. 7-Methylguanine (7-mGua), O6-Methylguanine (O6-mGua), guanine, and NNK will be purchased from Chemsyn Science Laboratories (Lenexa, Kans.).

The chemopreventative effect of the test compounds on NNK-induced DNA methylation in the lungs and liver of A/J mice will be evaluated using the procedures described by Morse et al., (*Cancer Res.* 49:549–553 (1989)). Groups of 3 to 6 mice will be administered cottonseed oil. Test compounds (80% MTD) dissolved in 0.3 mL cottonseed oil will be administered by gavage once every two days for a total of 3 doses. The dosages are those used for p-xyleneselenocyanate where maximum activity was observed. Tanaka et al., *Cancer Res.* 57:3644–3648 (1997). On the day of the third dose, intraperitoneal (ip) injection of NNK 10 µmol/0.1 mL isotonic saline/mouse will be given after 2 hours of the final gavage. The animals will be sacrificed by cervical dislocation at 4 hours folloing NNK dosing. DNA will be isloated from the excised livers and lungs according to the procedures in *Current Protocols in Molecular Biology*, Vol. 1, Unit 2.2, Frederick et al., eds., John Wiley and Sons, New York (1990). An aliquot of each purified hepatic DNA sample of all of each lung DNA sample will be subjected to neural thermal hydrolysis (100° C., 30 min) to release 7-mGua and guanine. The hydrolysates will be centrifuged and the pellets hydrolyzed in 0.1 N HCl (70° C., 30 min) to release $O^6$-mGua, and guanine will be quantitated by strong cation exchange HPLC column and fluorescence detection according to the method of Rouseff et al., (*Anal. Chem.* 52:1228–1233 (1980)). The identities of 7-mGua, $O^6$-mGua and guanine. Pre HPLC sample purification will be accomplished by the use of Gelman Acrodiscs (Gelman Science, Ann Arbor, Mich.). 7-mGua, $O^6$-mGua, and guanine will be confirmed by co-elution with authentic standards. The amount of $O^6$-mGua, calculated from a standard curve, will be expressed per 106 guanine bases. The significance of the experimental deviation from the control will be analyzed by the Student's "t" test. A P value of significance will be set at <0.05.

Example 14

Determination of Maximum Tolerated Dose (MTD) of Test Compounds

MTD is defined as the highest dose that causes no more than 10% body weight reduction as compared to those fed the control diet and does not induce mortality or external clinical signs of toxicity that would be predicted to shorten the natural life span of the animal. At 5 weeks of age, ten groups of female $CF_1$ or A/J mice will be fed AIN 76A semipurified diet and given 0.08, 0.015, 0.3, 0.6 and 1.12 mmol/kg body weight dose of test compounds alternate days for 1 week. All animals will be examined daily for any symptoms of toxicity. Body weight will be recorded twice weekly for 8 weeks. After 8 weeks the animals will be sacrificed and tissues will be examined grossly under the dissection microscope for any abnormalities that can be attributed to toxicity of the test agents.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A compound having formula I:

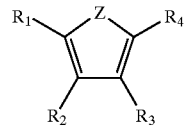

wherein:
$R_1$ is H, (alkylene)-SeCN, or a blocking group;
$R_2$ is H, (alkylene)-SeCN, or a blocking group;
$R_3$ is H, (alkylene)-SeCN, or a blocking group;
$R_4$ is (alkylene)-SeCN; and
Z is Se;
with the proviso that when $R_1=R_4=CH_2$-SeCN, at least one of $R_2$ and $R_3$ is not H.

2. The compound of claim 1 wherein $R_1$ is (alkylene)-SeCN.

3. A method for making the compound of claim 1 wherein $R_1=R_4 =CH_2$-SeCN; $R_2=R_3$=H; and Z=Se; the method comprising:
(a) reacting selenophene chloromethylether to yield the chlorinated heterocylic ring intermediate 2,5selenophenylbis(methylene)chloride and
(b) reacting the chlorinated heterocyclic ring intermediate with potassium selenocyanate to yield the compound of claim 1 wherein $R_1=R_4=CH_2$-SeCN; $R_2=R_3$=H; and Z=Se.

4. A method for making the compound of claim 1 wherein $R_1=R_2=R_3=H$; $R_4=CH_2\text{-SeCN}$; and $Z=Se$, the method comprising:

(a) reacting selenophene with phosphorous oxychloride and dimethylformamide to yield selenophene-2-carboxaldehyde;

(b) reacting selenophene-2-carboxaldehyde with hydrazine under reducing conditions to yield 2-methylselenophene;

(c) reacting 2-methylselenophene with a brominating reagent to yield 2-bromomethylselenophene; and (d) reacting 2-bromomethylselenophene with potassium selenocyanate to yield the compound of claim 1 wherein $R_1R_2=R_3=H$; $R_4=CH_2\text{-SeCN}$; and $Z=Se$.

5. A compound having formula II:

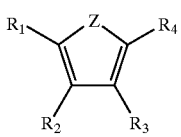

II wherein:

$R_1$ is H, (alkylene)-NCSe, or a blocking group;

$R_2$ is H, (alkylene)-NCSe, or a blocking group;

$R_3$ is H, (alkylene)-NCSe, or a blocking group;

$R_4$ is (alkylene)-NCSe; and

Z is Se.

6. The compound of claim 5 wherein $R_1$ is (alkylene)-NCSe.

7. The compound of claims 1, 2, 5 or 6 wherein at least one of $R_2$ and $R_3$ is H.

8. The compound of claims 1, 2, 5 or 6 wherein each of $R_2$ and $R_3$ is H.

9. The compound of claim 1, 2, 5 or 6 wherein $R_3$ is a blocking group.

10. The compound of claim 1 or 3 wherein the blocking group is selected from the group consisting of an alkyl group, an alkoxy group, an aryl group, an aryloxy group, an alkylmercapto group, an alkylene aryl group, a $CX_3$ group, and X; wherein X is F, Cl, or Br.

11. The compound of claim 10 wherein blocking group is selected from the group consisting of $CH_3$, $OCH_3$, $SCH_3$, $CX_3$ and X wherein X is selected from the group consisting of F, Cl and Br.

12. The compound of claim 11 wherein the blocking group is selected from the group consisting of $CH_3$, $OCH_3$, $SCH_3$, $CF_3$ and F.

13. A method for making the isoselenocyanate compound of claim 5 wherein $R_1=H$ or $CH_2NCSe$; $R_2=R_3=H$; $R_4=CH_2\text{-}NCSe$; and $Z=Se$; the method comprising photochemically isomerizing the corresponding selenocyanate compound in dry acetic acid to yield the isoselenocyanate.

14. A pharmaceutical composition comprising an active ingredient which is the compound selected from the group consisting of:

(a) a compound having formula I:

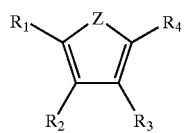

I wherein:

$R_1$ is H, (alkylene)-SeCN, or a blocking group;

$R_2$ is H, (alkylene)-SeCN, or a blocking group;

$R_3$ is H, (alkylene)-SeCN, or a blocking group;

$R_4$ is (alkylene)-SeCN; and

Z is Se;

(b) a compound having formula II:

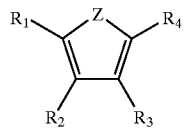

II wherein:

$R_1$ is H, (alkylene)-NCSe, or a blocking group;

$R_2$ is H, (alkylene)-NCSe, or a blocking group;

$R_3$ is H, (alkylene)-NCSe, or a blocking group;

$R_4$ is (alkylene)-NCSe; and

Z is Se.

15. The pharmaceutical composition of claim 14 further comprising a pharmaceutically acceptable carrier.

16. The pharmaceutical composition of claim 14 wherein the pharmaceutically acceptable carrier comprises a pharmaceutically acceptable salt.

17. The pharmaceutical composition of claim 14 formulated for parenteral administration.

18. The pharmaceutical composition of claim 14 formulated for topical administration.

19. A method for preventing the occurrence or progression of a cancer or a precancerous condition comprising administering to a mammal a chemopreventive composition comprising a compound selected from the group consisting of:

(a) a compound having formula I:

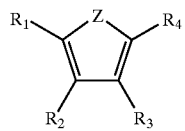

I wherein:

$R_1$ is H, (alkylene)-SeCN, or a blocking group;

$R_2$ is H, (alkylene)-SeCN, or a blocking group;

$R_3$ is H, (alkylene)-SeCN, or a blocking group;
$R_4$ is (alkylene)-SeCN; and
Z is Se;

(b) a compound having formula II:

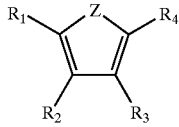

II wherein:
$R_1$ is H, (alkylene)-NCSe, or a blocking group;
$R_2$ is H, (alkylene)-NCSe, or a blocking group;
$R_3$ is H, (alkylene)-NCSe, or a blocking group;
$R_4$ is (alkylene)-NCSe; and
Z is Se.

20. The method of claim 19 wherein the chemopreventive compound is administered prophylactically to prevent the occurrence of a cancer or a precancerous condition in a mammal before, during or after exposure of the mammal to a known or suspected carcinogenic or procarcinogenic compound, agent or event.

* * * * *

UNITED STATES PATENT AND TRADEMARK OFFICE
CERTIFICATE OF CORRECTION

PATENT NO. : 6,703,524 B2
APPLICATION NO. : 10/081297
DATED : March 9, 2004
INVENTOR(S) : Lam et al.

It is certified that error appears in the above-identified patent and that said Letters Patent is hereby corrected as shown below:

On the title page item (56), OTHER PUBLICATIONS: line 1,
Delete the reference by Ausbel et al. and replace with --Ausubel et al., eds., Current Protocols in Molecular Biology, vol. 1, Unit 2.2, John Wiley & Sons, New York, 1990, Cover page, Publication page, Table of Contents and Unit 2.2.--

On the title page item (56), page 2, OTHER PUBLICATIONS: line 50,
Delete the reference by Ip et al. and replace with --Ip et al., "Cancer chemoprevention by aliphatic selenocyanates: effect of chain length on inhibition of mammary tumors and DMBA adducts," Carcinogenesis, 1995 Jan.; 16(1):35-38.--

On the title page item (56), page 2, OTHER PUBLICATIONS:
Delete the reference by Morimoto et al., and replace with --Morimoto et al., "N,N-Bis(trimethylsilyl) methoxymethylamine as a Convenient Synthetic Equivalent of Primary Aminomethylation of Organometallic Compounds," J. Chem. Soc. Chem. Commun., 1984;12:794-795.--

On the title page item (56), page 3, OTHER PUBLICATIONS: line 16,
Delete the first reference by Wattenberg, and replace with --Wattenberg, "Inhibition of Carcinogen-induced neoplasia by sodium cyanate, tert-Butyl Isocyanate, and Benzyl Isothiocyanate administered subsequent to carcinogen exposure," Cancer Res., 1981 Aug.; 41:2991-2994.--

On the title page item (56), page 3, OTHER PUBLICATIONS: line 30,
Delete the second reference by Yuryev et al., and replace with --Yuryev et al., "Chemistry of Selenophene IX. Condensation of Selenophene-2-Carboxaldehyde with methyl ketones, synthesis and reactions of 2-methylselenophene-5-carboxaldehyde," J. Gen. Chm. (USSR), 1957 Nov.; 27(11):3193-3197.--

On the title page item (56), page 3, OTHER PUBLICATIONS: line 39,
Delete the reference by Zhang et al. and replace with --Zhang et al., "A major inducer of anticarcinogenic protective enzymes from broccoli: Isolation and elucidation of structure," Proc. Natl Acad. Sc. USA, 1992 Mar.; 89(6):2399.--

UNITED STATES PATENT AND TRADEMARK OFFICE
CERTIFICATE OF CORRECTION

PATENT NO. : 6,703,524 B2
APPLICATION NO. : 10/081297
DATED : March 9, 2004
INVENTOR(S) : Lam et al.

It is certified that error appears in the above-identified patent and that said Letters Patent is hereby corrected as shown below:

In claim 3 at column 26, line 63, delete "2,5selenophenylbis(methylene)chloride" and insert --2,5-selenophenylbis(methylene)chloride--.

In claim 4 at column 27, line 17, delete "R1R2 = R3 = H" and insert
--R1 = R2 = R3 = H--.

In claim 10 at column 27, line 46, delete "The compound of claim 1 or 3" and insert
-- The compound of claim 1 or 5 --

Signed and Sealed this

Twenty-ninth Day of January, 2008

JON W. DUDAS
*Director of the United States Patent and Trademark Office*